United States Patent [19]

Ebetino et al.

[11] Patent Number: 5,770,586

[45] Date of Patent: Jun. 23, 1998

[54] QUATERNARY NITROGEN-CONTAINING PHOSPHONATE COMPOUNDS, PHARMACEUTICAL COMPOSITIONS, AND METHODS OF TREATING ABNORMAL CALCIUM AND PHOSPHATE METABOLISM AMD METHODS OF TREATING AND PREVENTING DENTAL CALCULUS AND PLAQUE

[75] Inventors: Frank Hallock Ebetino, Cincinnati, Ohio; Susan Mary Kaas, Sherburne, N.Y.; Marion David Francis, Cincinnati, Ohio; Dennis George Anthony Nelson; John Michael Janusz, both of West Chester, Ohio

[73] Assignee: The Procter & Gamble Company, Cincinnati, Ohio

[21] Appl. No.: 333,652

[22] Filed: Nov. 3, 1994

Related U.S. Application Data

[62] Division of Ser. No. 052,695, Apr. 30, 1993, Pat. No. 5,391,743, which is a continuation of Ser. No. 890,885, May 29, 1992, abandoned.

[51] Int. Cl.[6] .................. A61K 31/40; A61K 31/415; A61K 31/42; A61K 31/425

[52] U.S. Cl. .................. 514/91; 514/92; 514/94; 514/365; 514/374; 514/408; 514/306; 549/7; 549/6; 549/218; 548/119; 548/413

[58] Field of Search .................. 549/7, 6, 218; 548/119, 413; 514/91, 92, 94, 365, 374, 306, 408

[56] References Cited

U.S. PATENT DOCUMENTS

| | | | |
|---|---|---|---|
| 4,208,401 | 6/1980 | Bauman | 424/54 |
| 4,267,108 | 5/1981 | Blum et al. | 548/413 |
| 4,407,761 | 10/1983 | Blum et al. | 562/13 |
| 4,687,768 | 8/1987 | Benedict et al. | 514/102 |
| 4,746,654 | 5/1988 | Breliere et al. | 514/108 |
| 4,784,993 | 11/1988 | Bosies et al. | 514/93 |
| 4,868,164 | 9/1989 | Ebetino et al. | 514/80 |
| 4,876,247 | 10/1989 | Barbier et al. | 514/89 |
| 4,922,007 | 5/1990 | Kieczykowski et al. | 562/13 |
| 4,933,472 | 6/1990 | Isomura et al. | 549/218 |
| 4,939,130 | 7/1990 | Jaeggi et al. | 514/94 |
| 4,939,131 | 7/1990 | Benedict et al. | 514/102 |
| 4,971,958 | 11/1990 | Bosies et al. | 514/89 |
| 5,071,840 | 12/1991 | Ebetino et al. | 514/89 |
| 5,104,863 | 4/1992 | Benedict et al. | 514/80 |
| 5,137,880 | 8/1992 | Ebetino et al. | 514/80 |

FOREIGN PATENT DOCUMENTS

| | | |
|---|---|---|
| A-26738/88 | 6/1989 | Australia . |
| A-45467/89 | 5/1990 | Australia . |
| 0100718 | 2/1984 | European Pat. Off. . |
| 0170228 | 2/1986 | European Pat. Off. . |
| 0186405 | 7/1986 | European Pat. Off. . |
| 0298553 | 1/1989 | European Pat. Off. . |
| 0350002 | 1/1990 | European Pat. Off. . |
| 4011777 | 10/1990 | Germany . |
| 258695 | 10/1989 | Japan . |
| 8909775 | 10/1989 | WIPO . |
| WO 90/12017 | 10/1990 | WIPO . |
| WO 91/10646 | 7/1991 | WIPO . |

OTHER PUBLICATIONS

Chemical Abstracts 105: 134140, Bosies, 1986.
Chemical Abstracts 109:73664, 1988, Isomura.
Chemical Abstracts 110:95534, Sakamoto, 1988.
Chemical Abstracts 108:186996, Bosies, 1988.
Chemical Abstracts 112:198374, Sakamoto, 1989.
Medline #91231490, abstract of Levin, Hosptal Practice (Office Edition), vol. 26(5), 1991.
Medline #91246795, abstract of Gerber, Schweizerische Rundschau Fur Medizin Praxis, vol. 80(16), pp. 423–427, 1991.
Medline #91354901, abstract of Stewart, Current Opinion in Rheumatology, fol 3(3), pp. 380–387, 1991.
Amin, J of Lipid Research, vol. 33(11), pp. 1657–1663, 1992.

*Primary Examiner*—C. Warren Ivy
*Assistant Examiner*—D. Margaret M. Mach
*Attorney, Agent, or Firm*—Richard A. Hake; Carl J. Roof; Karen F. Clark

[57] ABSTRACT

The present invention relates to quaternary nitrogen-containing phosphate compounds, and the pharmaceutically-acceptable salts and esters thereof having the general structure:

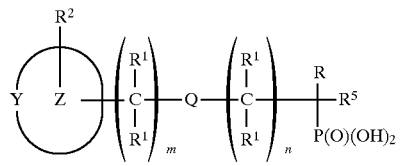

wherein:

Z is a saturated, unsaturated, or aromatic, monocyclic or polycyclic carbocycle or monocyclic or polycyclic heterocycle containing one or more heteroatoms selected from O, S, or N;

Y is $N^+(R^8)_2$ or $C(R^1)_2$ and when Y is $C(R^1)_2$, at least one $R^2$ must be $N^+(R^8)_3$;

$R^1$, $R^2$, $R^5$, and $R^8$ are defined in claim 1, m and n are integers from 0 to 10; m+n is from 0 to 10;

R is COOH; $PO_3H_2$; $SO_3H$; or $P(O)(OH)R_4$, wherein $R_4$ is substituted or unsubstituted alkyl of 1–8 carbons atoms.

The present invention further relates to pharmaceutical compostions containing a safe and effective amount of a compound of the present invention, and pharmaceutically-acceptable excipients. Finally, the present invention relates to methods for treating or preventing pathological conditions characterized by abnormal calcium and phosphate metabolism such as osteoporosis, rheumatoid arthritis, and osteoarthritis in humans or other mammals and to methods for treating or preventing dental calculus, plaque, and gingivitis.

31 Claims, No Drawings

QUATERNARY NITROGEN-CONTAINING PHOSPHONATE COMPOUNDS, PHARMACEUTICAL COMPOSITIONS, AND METHODS OF TREATING ABNORMAL CALCIUM AND PHOSPHATE METABOLISM AMD METHODS OF TREATING AND PREVENTING DENTAL CALCULUS AND PLAQUE

This is a division of application Ser. No. 08/052,695, filed on Apr. 30, 1993 now U.S. Pat. No. 5,391,745, which is a continuation of application Ser. No. 07/890,885, filed on May 29, 1992.

BACKGROUND OF INVENTION

This invention relates to novel quaternary nitrogen-containing phosphonate compounds, including bisphosphonates, phosphonoalkylphosphinates, phosphonocarboxylates, and phosphonosulfonates, preferably bisphosphonates and phosphonoalkylphosphinates. This invention also relates to pharmaceutical compositions containing these novel compounds as well as to a method of treating or preventing certain metabolic bone disorders characterized by abnormal calcium and phosphate metabolism by utilizing a compound or pharmaceutical composition of the present invention. Specifically, this invention relates to a method of treating or preventing osteoporosis and arthritis, especially rheumatoid arthritis and osteoarthritis by utilizing a compound or pharmaceutical composition of the present invention. This invention also relates to pharmaceutical compositions containing these novel compounds as well as to a method of treating or preventing dental calculus, plaque, and gingivitis. Specifically, this invention also relates to a method of treating or preventing dental calculus and plaque by utilizing a compound or pharmaceutical composition of the present invention.

Abnormal Phosphate and Calcium Metabolism

A number of pathological conditions which can afflict warm-blooded animals involves abnormal calcium and phosphate metabolism. Such conditions may be divided into two broad categories.

1. Conditions which are characterized by anomalous mobilization of calcium and phosphate leading to general or specific bone loss, such as osteoporosis and Paget's disease, or excessively high calcium and phosphate levels in the fluids of the body, such as hypercalcemia of tumor origin. Such conditions are sometimes referred to herein as pathological hard tissue demineralizations.

2. Conditions which cause or result from deposition of calcium and phosphate anomalously in the body, such as arthritis, including rheumatoid arthritis and osteoarthritis. These conditions are sometimes referred to herein as pathological calcifications.

The first category includes the most common metabolic bone disorder, osteoporosis; osteoporosis is a condition in which bone hard tissue is lost disproportionately to the development of new hard tissue. Osteoporosis can be generally defined as the reduction in the quantity of bone, or the atrophy of skeletal tissue. Marrow and bone spaces become larger, fibrous binding decreases, and compact bone becomes fragile. Osteoporosis can be subclassified as menopausal, senile, drug-induced (e.g. adrenocorticoid, as can occur in steroid therapy); disease-induced (arthritic and tumor), etc.; however, the manifestations are essentially the same. In general, there are two types of osteoporosis: primary and secondary. "Secondary osteoporosis" is the result of a separate identifiable disease process or agent. However, approximately 90% of all osteoporosis cases are "primary osteoporosis". Such primary osteoporosis includes postmenopausal osteoporosis, disuse osteoporosis, age-associated osteoporosis (affecting a majority of individuals over the age of 70 to 80), and idiopathic osteoporosis affecting middle-aged and younger men and women.

For some osteoporotic individuals, the loss of bone tissue is sufficiently great so as to cause mechanical failure of the bone structure. Bone fractures often occur, for example, in the hip and spine of women suffering from postmenopausal osteoporosis. Kyphosis (abnormally increased curvature of the thoracic spine) may also result.

The mechanism of bone loss in osteoporotics is believed to involve an imbalance in the process of "bone remodeling". Bone remodeling occurs throughout life, renewing the skeleton and maintaining the strength of bone. This remodeling involves the erosion and filling of discrete sites on the surface of bones, by an organized group of cells called "basic multicellular units" or "BMUs". BMUs primarily consist of "osteoclasts", "osteoblasts", and their cellular precursors. In the remodeling cycle, bone is resorbed at the site of an "activated" BMU by an osteoclast, forming a resorption cavity. This cavity is then filled with bone by an osteoblast.

Normally, in adults, the remodeling cycle results in a small deficit in bone, due to incomplete filling of the resorption cavity. Thus, even in healthy adults, age-related bone loss occurs. However, in osteoporotics, there may be an increase in the number of BMUs that are activated. This increased activation accelerates bone remodeling, resulting in abnormally high bone loss.

Although its etiology is not fully understood, there are many risk factors thought to be associated with osteoporosis. These include low body weight, low calcium intake, physical inactivity, and estrogen deficiency.

Current osteoporosis treatment consists primarily of calcium and estrogen administration.

The second category, involving conditions manifested by anomalous calcium and phosphate deposition, includes myositis ossificans progressiva, calcinosis universalis, and such afflictions as arthritis (including, for example, rheumatoid arthritis and osteoarthritis), neuritis, bursitis, tendonitis, and conditions which predispose involved tissue to deposition of calcium.

In addition to osteoporosis, bone loss can result from rheumatoid arthritis and osteoarthritis. Rheumatoid arthritis is a chronic, systemic and articular inflammatory disorder characterized by weakening of the joint capsules and ligaments, followed by destruction of cartilage, ligaments, tendon and bone, and a decrease in viscosity and other alterations in the synovial fluid. Rheumatoid arthritis symptoms include systemic weakness, fatigue, localized pain, stiffness and weakness and swelling and deformation of the joints of the body. Rheumatoid arthritis is most common in women in the fourth to sixth decade of life.

The pathogenesis of rheumatoid arthritis, leading to the destruction of the joints, is characterized by two phases: 1) an exudative phase involving the microcirculation and the synovial cells that allow an influx of plasma proteins and cellular elements into the joint and 2) a chronic inflammatory phase occurring in the sub-synovium and subchondral bone, characterized by pannus (granulation tissue) formation in the joint space, bone erosion, and cartilage destruction. The pannus may form adhesions and scar tissue which causes the joint deformities characteristic of rheumatoid arthritis.

The etiology of rheumatoid arthritis remains obscure. Infectious agents such as bacteria and viruses have been implicated. A current hypothesis is that the Epstein-Barr (EBV) virus is a causative agent for rheumatoid arthritis.

Current rheumatoid arthritis treatment consists predominantly of symptomatic relief by administration of non-steroidal anti-inflammatory drugs. Non-steroidal anti-inflammatory drug treatment is mainly effective in the early stages of rheumatoid arthritis; it is unlikely it will produce suppression of joint inflammation if the disease is present for more than one year. Gold, methotrexate, immunosuppressants and orticosteroids have been tried with limited success.

On the other hand, osteoarthritis is an inherently non-inflammatory disorder of the movable joints characterized by deterioration and abrasion of articular cartilage, as well as by formation of new bone at the joint surface. As osteoarthritis progresses, the surface of the articular cartilage is disrupted and wear particles gain access to the synovial fluid which in turn stimulates phagocytosis by macrophage cells. Thus, an inflammatory response is eventually induced in osteoarthritis.

Common clinical symptoms of osteoarthritis include cartilaginous and bony enlargements of the finger joints and stiffness on awakening, and painful movement. Common symptomatic treatments for osteoarthritis include analgesics, anti-inflammatories, steroids, and physical therapy.

Dental Calculus and Plague

Dental plaque is a rough sticky film on the teeth that is made up of saliva, bacteria and food particles which adheres tenaciously to teeth at points of irregularity or discontinuity. Plaque can cause gingivitis and tooth decay, and may form the basis of calculus, also known as tartar, a hard calcified deposit, if permitted to accumulate.

Calculus is formed when mineral salts from saliva, primarily phosphorus and calcium, are embedded into the dental plaque, forming crusty hard deposits. Calculus tends to form near the orifices of the salivary ducts: on the lingual surfaces of the lower incisors and on the distal surfaces of the upper molars.

As the mature calculus develops, it becomes visibly white or yellowish in color unless stained or discolored by some extraneous agent. In addition to being unsightly and undesirable aesthetically, calculus is continually covered by plaque. The toxins in plaque and calculus irritate the gingiva causing inflammation and recession of the gums which can lead to other complications.

A wide variety of chemical and biological agents have been suggested in the art to retard calculus formation or to remove calculus after it is formed. The chemical approach to calculus inhibition generally involves crystal growth inhibition which prevents the calculus from forming. Chelation of calcium ions breaks down mature calculus by removing calcium but it is not desirable because it can also remove normal calcified tissue. Mechanical removal of this material periodically by the dentist is, of course, routine dental office procedure.

A variety of phosphonic acid derivatives have been proposed for use in the treatment and prophylaxis of diseases involving abnormal calcium and phosphate metabolism. For example, numerous references, all incorporated by reference herein, disclose compositions containing polyphosphonates, in particular diphosphonates such as ethane-1-hydroxy-1,1-diphosphonic acid ("EHDP"), and their use in inhibiting anomalous deposition and mobilization of calcium and phosphate in animal tissue: U.S. Pat. No. 3,683,080, issued Aug. 8, 1972 and U.S. Pat. No. 4,230,700, issued Oct. 28, 1980, both to Francis, and U.S. Pat. No. 4,868,164 to Ebetino, issued Sep. 19, 1989. Numerous other references describe heterocyclic substituted phosphonic acids useful for the treatment of osteoporosis and/or arthritis, and are hereby incorporated by reference herein: U.S. Pat. No. 5,071,840, to Ebetino, et al., issued Dec. 10, 1991; U.S. Pat. No. 4,868,164, to Ebetino, et al., issued Sep. 19, 1989; U.S. Pat. No. 5,104,863, to Benedict, et al., issued Apr. 14, 1992; U.S. Pat. No. 4,267,108, to Blum et al., issued May 12, 1981; U.S. Pat. No. 4,746,654 to Breliere et al., issued May 24, 1988; U.S. Pat. No. 4,876,247 to Barbier, et al., issued Oct. 24, 1989, and European Patent Application Publication No. 100,718, of Breliere, published Feb. 15, 1984; European Patent Application Publication No. 170,228, of Boehringer Mannheim GmbH, published Feb. 5, 1986; European Patent Application Publication No. 186,405, of Benedict and Perkins, published Jul. 2, 1986; European Patent Application Publication No. 298,553, of Ebetino, published Jan. 11, 1989; U.S. Pat. No. 4,754,993, to Bosies, et al., issued Nov. 15, 1988; U.S. Pat. No. 4,939,130, to Jaeggi, et al., issued Jul. 3, 1990; U.S. Pat. No. 4,971,958 to Bosies, et al., issued Nov. 20, 1990; WO 90/12017, Dunn, et al. published Oct. 18, 1990; WO 91/10646, Youssefyeh, R., et al. published Jul. 25, 1991; AU-A-26738/88, Jaeggi, publication date Jun. 15, 1989; AU-A-45467/89 of Ciba-Geigy, publication date May 31, 1990.

Finally, U.S. Pat. No. 4,208,401 to Bauman, issued Jun. 17, 1980, discloses non-heterocyclic ring substituted quaternary ammonium bisphosphonates useful as anti-calculus agents.

DE 40 11 777 to Jaeggi, K., disclosed Oct. 18, 1990; (DE '777) discloses a heterocyclic ring substituted diphosphonate wherein said heterocyclic ring can be lower alkyl substituted. Said heterocyclic ring is bridged to the phosphonic acid group via a quaternary non-ring nitrogen atom. DE '777 also discloses that the compounds produce pronounced inhibition of bone resorption and thus are useful in treating osteoporosis, inflammatory and degenerative joint diseases, peridontitis, and hyperparathyroidism. The disclosures of these patents and applications are incorporated by reference herein.

None of these references, however, disclose the utility of a heterocyclic phosphonate compound containing a quaternized nitrogen in preventing and treating both osteoporosis, arthritis, or in preventing dental calculus, plaque, and gingivitis.

The compounds of the present invention have osteoprotective activity at the site of joint destruction in arthritis conditions and have that activity as an additional benefit in the treatment of arthritis over the above merely relieving the symptoms of inflammation. The term "osteoprotective activity" as used herein means disease-modifying activity on bone and surrounding soft tissue at the site of joint destruction.

It has been surprisingly discovered that the heterocyclic phosphonate compounds of the present invention, which contain a nitrogen atom in the compound that is quaternized, have more potent bone antiresorptive activity, and therapeutic utility in treating and preventing osteoporosis, arthritis (including rheumatoid arthritis and osteoarthritis), and dental calculus and plaque, than heterocyclic-ring containing phosphonate compounds which do not contain a quaternized nitrogen atom. Moreover, the compounds of the present invention exhibit unusual solubility properties. Thus, the compounds of the present invention may be more readily orally absorbed. The more readily absorbed a compound, the more effective it may be at lower doses. Lower doses are generally preferable because undesirable side effects are decreased.

It is therefore an object of the present invention to provide new more potent, compounds which are useful in osteoporosis therapy, and as anti-arthritic agents (especially useful in the treatment of osteoarthritis and rheumatoid arthritis) and in treating and preventing dental calculus and plaque. It is a further object of the present invention to provide pharmaceutical compositions useful for the treatment and prophylaxis of osteoporosis and arthritis, especially rheumatoid arthritis and osteoarthritis. In addition, it is an object of the present invention to provide methods for treating or preventing osteoporosis, rheumatoid arthritis and osteoarthritis. It is also an object of the present invention to provide methods for treating or preventing dental calculus and plaque.

These and other objects of the present invention will become apparent from the detailed disclosure of the present invention provided hereinafter.

SUMMARY OF THE INVENTION

The present invention relates to quaternary nitrogen-containing heterocyclic phosphonates compounds, and the pharmaceutically-acceptable salts and esters thereof and having the general structure:

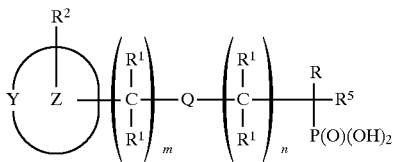

wherein m and n are integers from 0 to 10; m+n is from 0 to 10;

(a) Q is a covalent bond or a moiety selected from O, S, $NR^1$;

(b) Y is $N^+(R^8)_2$ or $C(R^1)_2$ and when Y is $C(R^1)_2$, at least one $R^2$ must be $N^+(R^8)_3$;

(c) Z is a saturated, unsaturated, or aromatic, monocyclic or polycyclic carbocycle or heterocycle containing one or more heteroatoms selected from O, S, or N;

(d) R is COOH; $PO_3H_2$; $SO_3H$; or $P(O)(OH)R_4$, wherein $R_4$ is substituted or unsubstituted alkyl of 1–8 carbon atoms;

(e) each $R_1$ is selected from the group consisting of nil; $SR^6$; $R^9SR^6$; hydrogen; hydroxy; substituted or unsubstituted $C_1$–$C_8$ alkyl; —$OR^3$; —$CO_2R^3$; —$O_2CR^3$; —$NR^3{}_2$; —$N(R^3)C(O)R^3$; —$C(O)N(R^3)_2$; halogen; —$C(O)R^3$; arylalkyl; nitro; substituted or unsubstituted aryl, and combinations thereof.

(f) each $R_2$ is one or more substituents on the Z moiety independently selected from the group consisting of $N^+(R^8)_3$; $SR^6$; $R^9SR^6$; hydrogen; substituted or unsubstituted $C_1$–$C_8$ alkyl; —$OR^3$; —$CO_2R^3$; —$O_2CR^3$; —$NR^3{}_2$; —$N(R^3)C(O)R^3$; —$C(O)N(R^3)_2$; halogen; hydroxy; —$C(O)R^3$; arylalkyl; nitro; substituted or unsubstituted aryl;

(g) each $R_3$ is independently selected from the group consisting of hydrogen, substituted or unsubstituted alkyl having from 1–8 carbon atoms, and $R^9SR^6$;

(h) $R_5$ is selected from the group consisting of hydrogen; halogen; $SR^6$; $R^9SR^6$; amino; hydroxy; and substituted or unsubstituted $C_1$–$C_8$ alkyl;

(i) each $R^6$ is independently selected from the group consisting of H; —$C(O)R^7$; —$C(S)R^7$; —$C(O)NR^7{}_2$; —$C(S)N(R^7)_2$; —$C(S)OR^7$; —$C(O)OR^7$; wherein $R^7$ is hydrogen or substituted or unsubstituted $C_1$–$C_8$ alkyl.

(j) each $R^8$ is independently selected from the group consisting of nil, substituted or unsubstituted alkyl having 1–35 carbon atoms, substituted or unsubstituted phenyl, benzyl, or $R^9SR^6$; and (k) $R^9$ is a substituted or unsubstituted $C_1$–$C_8$ alkyl;

In this general structure, Z is a monocyclic or polycyclic, saturated or unsaturated heterocyclic or carbocyclic moiety, and Y is $N+(R^8)_2$ or $C(R^1)_2$. In addition, m and n and m +n are integers from about 0 to about 10 and Q is a covalent bond or a moiety selected from the group consisting of oxygen, sulfur, or $NR^1$. Further in this general structure, each $R^1$ is independently selected from a variety of substituents, most preferably $R^9SR^6$ and hydrogen. Each $R^2$ is a substituent on the heterocyclic or carbocyclic ring, selected from a variety of substituents, preferably $N^+C(R^8)_3$, $C_1$–$C_8$ alkyl, amino, hydroxy, halide, alkoxy or $R^9SR^6$. When Y is $C(R^1)_2$, at least one $R^2$ must be $N^+(R^8)_3$. Each R is independently selected from the group consisting of COOH, $SO_3H$, $PO_3H_2$, and $P(O)(OH)R_4$, wherein $R_4$ is a lower alkyl group. $R_5$ is selected from a variety of substituents, the most preferred being hydrogen, hydroxy, halogen and amino. $R^6$ is selected from a variety of substituents, the most preferred being H and —$C(O)R^7$ and —$C(S)R^7$, wherein $R^7$ is substituted or unsubstituted $C_1$–$C_8$ alkyl. $R^8$ is selected from a substituted or unsubstituted $C_1$–$C_{35}$ alkyl, preferably a $C_1$–$C_8$ alkyl; substituted or unsubstituted phenyl; benzyl; or $R^9SR^6$. $R^9$ is substituted or unsubstituted $C_1$–$C_8$ alkyl, preferably a $C_1$–$C_4$ alkyl.

The present invention further relates to pharmaceutical compositions containing a safe and effective amount of a compound of the present invention, and pharmaceutically-acceptable excipients. Finally, the present invention relates to methods for treating or preventing pathological conditions characterized by abnormal calcium and phosphate metabolism such as osteoporosis, rheumatoid arthritis, and osteoarthritis in humans or other mammals and to methods for treating or preventing dental calculus, plaque and gingivitis. This method comprises administering to a human or other mammal in need of such treatment a safe and effective amount of a compound or composition of the present invention.

Definitions and Usage of Terms

The following is a list of definitions for terms used herein.

"Heteroatom" is a nitrogen, sulfur, or oxygen atom. Groups containing one or more heteroatoms may contain different heteroatoms.

"Alkyl" is an unsubstituted or substituted, straight-chain or branched, saturated or unsaturated hydrocarbon chain, said hydrocarbon chain may be saturated, having 1 to 8 carbon atoms, and preferably, unless otherwise stated, from 1 to 4 carbon atoms; said hydrocarbon chain may be unsaturated, having 2 to 8 carbon atoms, and preferably, unless otherwise stated, 2 to 4 carbon atoms. Accordingly, the term "alkyl", as used herein, encompasses alkenyl hydrocarbon unsaturated chains having at lease one olefinic double bond and alkynyl hydrocarbon unsaturated chains having at least one triple bond. Preferred alkyl groups include, but are not limited to, methyl, ethyl, propyl, isopropyl, and butyl.

"Carbocyclic ring" or "Carbocycle" as used herein is an unsubstituted or substituted, saturated, unsaturated or aromatic, hydrocarbon ring. Carbocycles may be monocyclic or polycyclic; Monocyclic rings generally contain from 3 to 8 atoms, preferably 5 to 7 atoms; polycyclic rings containing two ring contain 6 to 16, preferably 10 to 12, atoms and those with three rings generally contain 13 to 17, preferably 14 to 15, atoms.

"Heteroalkyl" is an unsubstituted or substituted, saturated chain having from 3 to 8-members and comprising carbon atoms and one or two heteroatoms.

"Heterocyclic ring" or "Heterocycle" as used herein is an unsubstituted or substituted, saturated, unsaturated or aromatic ring comprised of carbon atoms and one or more heteroatoms in the ring. Heterocyclic rings may be monocyclic or polycyclic rings. Monocyclic rings generally contain from 3 to 8 atoms, preferably 5 to 7, atoms. Polycyclic ring systems consisting of two rings generally contain 6 to 16, preferably from 10 to 12, atoms. Polycyclic ring systems consisting of three rings generally contain 13 to 17 atoms, preferably 14 to 15 atoms. A heterocyclic ring moiety may consist of heterocycles or heterocycles and carbocycles. Each heterocyclic ring moiety must have at least one nitrogen atom. Unless otherwise stated any additional heteroatoms may be independently chosen from nitrogen, sulfur, and oxygen.

"Aryl" is an aromatic carbocyclic ring. Preferred aryl groups include, but are not limited to, phenyl, tolyl, xylyl, cumenyl, and naphthyl.

"Heteroaryl" is an aromatic heterocyclic ring. Preferred heteroaryl groups include, but are not limited to, thienyl, furyl, pyrrolyl, pyridinyl, pyrazinyl, oxazolyl, thiazolyl, quinolinyl, pyrimidinyl, and tetrazolyl.

"Alkoxy" is an oxygen atom having a hydrocarbon chain substituent, where the hydrocarbon chain is an alkyl or alkenyl (e.g., —O-alkyl or -O-alkenyl). Preferred alkoxy groups include, but are not limited to, methoxy, ethoxy, propoxy, and alkyloxy.

"Hydroxyalkyl" is a substituted hydrocarbon chain which has a hydroxy substituent (e.g., —OH), and may have other substituents. Preferred hydroxyalkyl groups include, but are not limited to, hydroxyethyl and hydroxypropyl.

"Carboxyalkyl" is a substituted hydrocarbon chain which has a carboxy substituent (e.g. COOH) and may have other substituents. Preferred carboxyalkyl groups include carboxymethyl, carboxyethyl, and their acids and esters.

"Aminoalkyl" is a hydrocarbon chain (e.g. alkyl) substituted with an amine moiety (e.g., NH-alkyl-) such as aminomethyl.

"Alkylamino" is an amino moiety having one or two alkyl substituents (e.g., —N-alkyl) such as dimethylamino.

"Alkenylamino" is an amino moiety having one or two alkenyl substituents (e.g., —N-alkenyl).

"Alkynalamino" is an amino moiety having one or two alkynyl substituents (e.g., —N-alkynyl).

"Alkylimino" is an imino moiety having one or two alkyl substituents (e.g., —N-alkyl-).

"Arylalkyl" is an alkyl moiety substituted with an aryl group. Preferred arylalkyl groups include benzyl and phenylethyl.

"Arylamino" is an amine moiety substituted with an aryl group (e.g., —NH-aryl).

"Aryloxy" is an oxygen atom having an aryl substituent (e.g., —O-aryl).

"Acyl" or "carbonyl" is a carbon to oxygen double bond, e.g. R—C(=O). Preferred acyl groups include, but are not limited to, acetyl, propionyl, butanoyl, and benzoyl.

"Acyloxy" is an oxygen atom having an acyl substituent (e.g., —O-acyl); for example, —O—C(=O)-alkyl.

"Acylamino" is an amino moiety having an acyl substituent (e.g., —N-acyl); for example, —NH—(C=O)-alkyl.

"Halo", "halogen", or "halide" is a chloro, bromo, fluoro, or iodo atom radical. Chloro, bromo, and fluoro are preferred halides.

As referred to herein, a "lower" hydrocarbon moiety (e.g., "lower" alkyl) is a hydrocarbon chain comprised of from, unless otherwise stated, 1 to 6, preferably from 1 to 4, carbon atoms.

Also, as used herein, the term "thio-substituent" ($SR^6$ or $R^9SR^6$) includes thiols [—SH] where $R^6$=H; thioesters [—SC(O)$R^7$] where $R^6$=C(O)$R^7$; dithioesters [—SC(S)$R^7$] where $R^6$=C(S)$R^7$; thiocarbamates [—SC(O)N($R^7$)$_2$] where $R^6$=C(O)N($R^7$)$_2$; dithiocarbamates [—SC(S)N($R^7$)$_2$] where $R^6$=C(S)N($R^7$)$_2$; thiocarbonates [=SC(O)O$R^7$] where $R^6$=C(O)O$R^7$; and dithiocarbonates [—SC(S)O$R^7$] where $R^6$=C(S)O$R^7$. $R^7$ is hydrogen or substituted or unsubstituted $C_1$–$C_8$ alkyl. Any of the $SR^6$ substituents may themselves be substituted with an $R^9$ moiety, where $R^9$ is a substituted or unsubstituted $C_1$–$C_8$ alkyl. Accordingly, additional thio-substituents denoted by $R^9SR^6$ are alkylthiols, alkylthioesters, alkyldithioesters, alkylthiocarbamates, alkyldithiocarbamates, alkylthiocarbonates, and alkyldithiocarbonates.

The terms "bisphosphonate" or "bisphosphonic acid" as used herein, relate to those phosphonates or phosphonic acids that have two phosphonate groups attached to the same carbon atom and are used interchangeably with the terms "diphosphonate" and "diphosphonic acids". Using the structures described herein, the moiety R is $PO_3H_2$.

A "pharmaceutically-acceptable" salt is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987, hereby incorporated by reference herein. Preferred cationic salts include the alkali-metal salts (such as sodium and potassium), and alkaline earth metal salts (such as magnesium and calcium). Preferred anionic salts include the halide (such as chloride), acetate and phosphate salts.

A "biohydrolyzable ester" is an ester of the quaternary nitrogen-containing heterocyclic phosphonate compounds that does not interfere with the therapeutic activity of the compounds, or that is readily metabolized by a human or other mammal. Many such esters are known in the art, as described in World Patent Publication 87/05297, Johnston et al., published Sep. 11, 1987, and hereby incorporated by reference herein. Such esters include lower alkyl esters, lower acyloxyalkyl esters (such as acetoxylmethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters, and acylamino alkyl esters (such as acetamidomethyl esters).

As defined above and as used herein, substituent groups may themselves be substituted. Such substitution may be with one or more substituents. Such substituents include, but are not limited to, those listed in C. Hansch and A. Leo, *Substituent Constants for Correlation Analysis in Chemistry and Biology* (1979), hereby incorporated by reference herein. Preferred substituents include, but are not limited to, alkyl, alkenyl, alkoxy, hydroxy, oxo, amino, aminoalkyl (e.g. aminomethyl, etc.), cyano, halo, carboxy, alkoxyacetyl (e.g. carboethoxy, etc.), thio, thiol, aryl, cycloalkyl, heteroaryl, heterocycloalkyl (e.g., piperidinyl, morpholinyl, piperazinyl, pyrrolidinyl, etc.), imino, thioxo, hydroxyalkyl, aryloxy, arylalkyl, and combinations thereof.

DETAILED DESCRIPTION OF THE INVENTION

Quaternary Nitrogen-Containing Heterocyclic Phosphonate Compounds

The compounds of the present invention are quaternary nitrogen-containing phosphonate compounds, and the pharmaceutically-acceptable salts and esters thereof, in which the phosphonic acid-containing carbon atom is linked to a carbon atom in a monocyclic or polycyclic heterocyclic or carbocycylic ring moiety. The linkage from the phosphonic acid-containing carbon atom to the heterocyclic or carbocyclic ring moiety may be direct through a covalent bond (preferably a single bond), or by a chain of a length of 1 to 10 atoms. If the linkage is via a linking chain, this chain may be all carbon atoms, a nitrogen atom or nitrogen-containing chain, an oxygen atom or oxygen-containing chain, or a sulfur atom or sulfur-containing chain. The carbon and nitrogen atoms in the linking chains may, independently, be unsubstituted or substituted with one or more substituents selected from methyl, ethyl, propyl, $SR^6$ and $R^9SR^6$. Unsubstituted carbon and nitrogen atoms in the chain are preferred. Also preferred are chains one atom in length, i.e., —$CH_2$—, —NH—, —S—, and —O—.

For the compounds in which a sulfur, nitrogen or oxygen atom in the linking chain is bonded to the heterocyclic or carbocyclic ring moiety, this sulfur, nitrogen or oxygen atom is bonded to the ring at a carbon atom and not bonded directly to the ring's nitrogen atom. For the compounds in which a carbon in the linking chain is bonded to the heterocyclic or carbocyclic ring, this carbon can be bonded to the ring at the carbon atom or directly to the ring's nitrogen atom.

The carbon atom which has the phosphonic acid group attached to it may be unsubstituted (i.e., a hydrogen atom), or substituted. The phosphonic acid carbon may contain two phosphonate groups, rendering a bisphosphonate compound; a phosphonate group and an carboxylate group, rendering a phosphonocarboxylate compound; a phosphonate group and a sulfonate group, rendering a phosphonosulfonate compound, a phosphinate group and a phosphonate group rendering a phosphonoalkylphosphinate compound. Furthermore, the carbon atoms in the Z moiety may be unsubstituted or substituted independently with one or more substituents. The nitrogen atom in the heterocycle ring may ($Y=N^+(R^8)_2$) or may not ($Y=C(R^1)_2$) be quarternized, but the heterocyclic-containing phosphonate compound must contain a quarternized nitrogen atom in at least one of the Y or $R^2$ substituents. Accordingly, either $Y=N^+(R^8)_2$ or at least one of $R^2=N^+(R^8)_3$.

Thus, the quaternary nitrogen-containing saturated and unsaturated heterocyclic and carbocyclic phosphonate compounds of the present invention, and the pharmaceutically-acceptable salts and esters thereof, have the general structure:

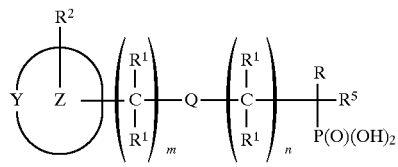

In this general structure, Z is a quaternary ring nitrogen-containing, saturated, unsaturated, or aromatic, monocyclic or polycyclic carbocyclic or heterocyclic ring moiety. Said heterocyclic ring moiety contains one or more additional heteroatoms selected from oxygen, sulfur or nitrogen.

The Z moiety of the present invention may be a heterocyclic ring moiety; said heterocyclic ring moiety may have one or more heteroatoms selected from O, S, or N; at least one of may be a quaternary nitrogen. The Z moiety may be a monocyclic heterocyclic or carbocyclic ring moiety having 3–8 atoms or it may be a polycyclic heterocyclic or carbocyclic ring moiety having 7–17 atoms. Said polycyclic ring moiety may contain either two or more heterocycles, two or more carbocycles, one carbocycle and one or more heterocycles, or one heterocycle and one or more carbocyclic rings. Preferred Z heterocyclic ring moieties contain at least one quaternized nitrogen atom and preferred monocyclic Z moieties are: pyrimidinium, piperidinium, pyridinium, quinolinium, pyrrolopyridinium, quinoxalinium, and inidazopyridinium.

In this general structure, Y is a member of the cyclic Z moiety and may be $N^+(R^8)_2$ or $C(R^1)_2$. Q is a covalent bond, (preferably a single bond) or a moiety selected from oxygen, —$NR^1$—, or sulfur. Further, m and n and m+n are integers from 0 to 10, with m+n=0 or 1 being preferred. Q can be a covalent bond, oxygen, sulfur, or —$NR^1$; preferred for Q is a covalent bond; m+n=0, 1, 2 or 3. The R moieties described herein may be COOH; $SO_3H$; $PO_3H_2$ or $P(O)(OH)R^4$, where $R^4$ is $C_1$–$C_8$ alkyl; preferably R is $PO_3H_2$ or $P(O)(OH)R^4$.

The $R^1$ moiety is selected from nil, $SR^6$, $R^9SR^6$ hydrogen; halogen; substituted and unsubstituted $C_1$–$C_8$ alkyl, arylalkyl, nitro, substituted and unsubstituted aryl, hydroxy, —$OR^3$, —$CO_2R^3$, —$O_2CR^3$, —$NR^3_2$, —$N(R^3)C(O)R^3$, —$C(O)N(R^3)_2$, —$C(O)R^3$, and combinations thereof; wherein $R_3$ is hydrogen, alkyl having 1–8 carbon atoms and $R^9SR^6$ wherein $R^9$ is a $C_1$–$C_8$ alkyl. $R^6$ is H, —$C(O)R^7$, —$C(S)R^7$, —$C(O)NR^7$, —$C(S)NR^7$, —$C(S)OR^7$, —$C(O)(OR)^7$ wherein $R^7$ is nil, hydrogen or substituted or unsubstituted $C_1$–$C_8$ alkyl. Further, when a quaternary nitrogen-containing phosphonate compound is thio-substituted, the preferred $R^6$ is H, —$C(S)R^7$ or —$C(O)R^7$.

However, when n=0 and Q is oxygen, sulfur or nitrogen, then $R^5$ is selected from hydrogen, $R^9SR^6$, or alkyl having from 1 to 8 carbon atoms.

Preferred $R^1$ is selected from $SR^6$, $R^9SR^6$, hydrogen, chloro, methyl, ethyl, hydroxy, unsubstituted amino, (N-methyl)amino, (N, N-dimethyl)amino, —$CO_2H$ and the pharmaceutically-acceptable salts thereof, —$CO_2CH_3$ and —$CONH_2$. More preferred $R^1$ is selected from $SR^6$, $R^9SR^6$, hydrogen, methyl, chloro, amino, and hydroxy. Most preferred $R_1$ is $SR^6$, $R^9SR^6$, hydrogen, hydroxy, or amino.

The heterocyclic and carbocyclic ring moieties in the compounds of the present invention may be unsubstituted or substituted on the carbon atoms independently with one or more substituents ($R^2$). The $R^2$ groups may be on the same carbon atom, or on different carbon atoms of the ring moiety.

Thus, the $R^2$ groups are substituents on one or more carbon atoms of the ring moiety, independently selected from $N^+(R^8)_3$; $SR^6$; $R^6SR^6$, hydrogen; hydroxy; halogen; alkyl having from 1 to 8 carbon atoms; $-OR^3$, $-CO_2R^3$; $-O_2CR^3$; $-NR^3{}_2$; $-N(R^3)C(O)R^3$; $-C(O)N(R^3)_2$; $-C(O)R^3$, nitro, arylalkyl, substituted and unsubstituted aryl, and combinations thereof; wherein $R_3$ is hydrogen, substituted or unsubstituted alkyl or $R^9SR^6$.

Preferred $R^2$ substituents are independently selected from $N^+(R^8)_3$; $SR^6$, $R^9SR^6$, hydrogen, methyl, ethyl, hydroxy, unsubstituted amino, (N-methyl)amino, (N,N-dimethyl) amino, chloro, methoxy, ethoxy, nitro, $-CO_2H$, $-CO_2CH_3$, $-CONH_2$, and combinations thereof. More preferred $R^2$ substituents are independently selected from $SR^6$, $R^9SR^6$, hydrogen, methyl, amino, chloro, methoxy, hydroxy and combinations thereof. Most preferred $R^2$ substituents are independently selected from $R^9SR^6$, $SR^6$, hydrogen, amino, and methyl.

$R_5$ is selected from the group consisting of hydrogen; halogen; substituted or unsubstituted alkyl having from 1 to 8 carbon atoms; $R^9SR^6$; hydroxy and amino. When n=0 and Q is oxygen, sulfur or nitrogen then $R^5$ is selected from the group consisting of hydrogen; substituted or unsubstituted alkyl having from 1 to 8 carbon atoms or $R^9SR^6$.

Each $R^8$ moiety is independently selected from the group consisting of nil; substituted or unsubstituted alkyl having 1–35 carbons; phenyl, benzyl, or $R^9SR^6$. In this general structure, the $R^8$ substituent quarternizes the nitrogen heteroatom of the Z moiety (when $Y=N^+(R^8)_2$). The Z moiety, as described hereinbefore, can be a carbocycle or a heterocycle and can be a either saturated, unsaturated or aromatic. Whether a heterocyclic Z moiety is saturated, unsaturated or aromatic will determine the $R^8$ substituents needed to quarternize the nitrogen heteroatom, when $Y=N^+(R^8)_2$. When the Z moiety is an unsaturated or aromatic monocyclic or polycyclic heterocyclic ring moiety, the heterocyclic ring nitrogen is quarternized with only one $R^8$ substituent. Thus, when the Z moiety is an unsaturated or aromatic monocyclic or polycyclic heterocyclic ring moiety, one $R^8$ moiety can be nil. When the Z moiety is a saturated monocyclic or polycyclic heterocyclic ring moiety, the heterocyclic ring nitrogen is quarternized with two $R^8$ substituents. Thus, when the Z moiety is a saturated monocyclic or polycyclic heterocyclic ring moiety, neither $R^8$ can be nil in order to quarternize the heterocyclic ring nitrogen. As stated above at least one of Y or $R^2$ must contain a quaternized nitrogen atom, accordingly, when Y is $C(R^1)_2$, at least one of $R^2$ must be $N^+(R^8)_3$. Introduction of an $R^8$ moiety at the nitrogen heteroatom results in the formation of the quaternary nitrogen-containing moiety suitable as an $R^2$ substituent or as Y.

Preferred $R^8$ for compounds of the present invention useful in treating or preventing disorders of calcium and phosphate metabolism is substituted or unsubstituted alkyl having 1–10 carbons and $R^9SR^6$. Preferred $R^8$ for compounds of the present invention useful in treating or preventing dental calculus, plaque, and gingivitis is unsubstituted or substituted alkyl having 10–20 carbons.

Furthermore, in the hereinbefore general structures, when m=0 and Q is oxygen, nitrogen or sulfur, then the bonding of the Q moiety to a nitrogen-containing heterocyclic (Z) moiety is preferably limited as follows. The Q moiety is bonded to the heterocycle ring at a carbon atom and is not bonded directly to a nitrogen atom in the heterocycle ring.

The preferred diphosphonopyridinium compounds of the present invention may have the following general structure:

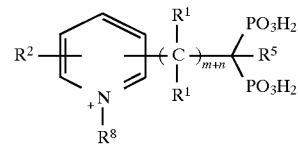

Also preferred are diphosphonopyridinium compounds wherein the linking chain has a heteroatom, i.e., Q=S, O, or $NR^1$.

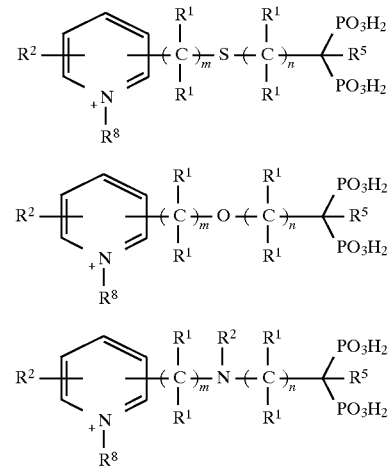

Preferred compounds of the present invention wherein Z is a polycyclic heterocycle include those compounds having the following structure:

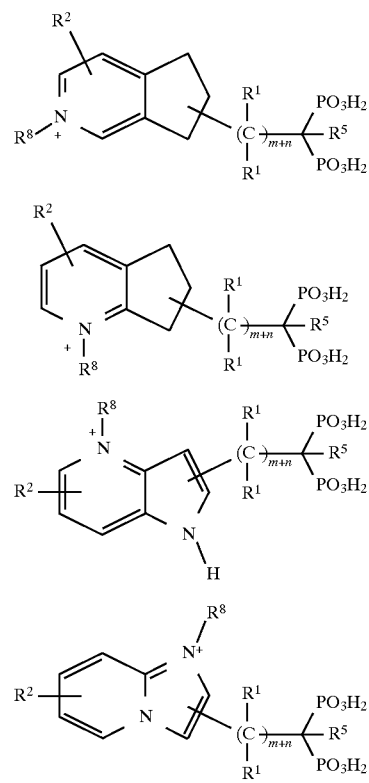

Compounds of the present invention may also have the following general structure:

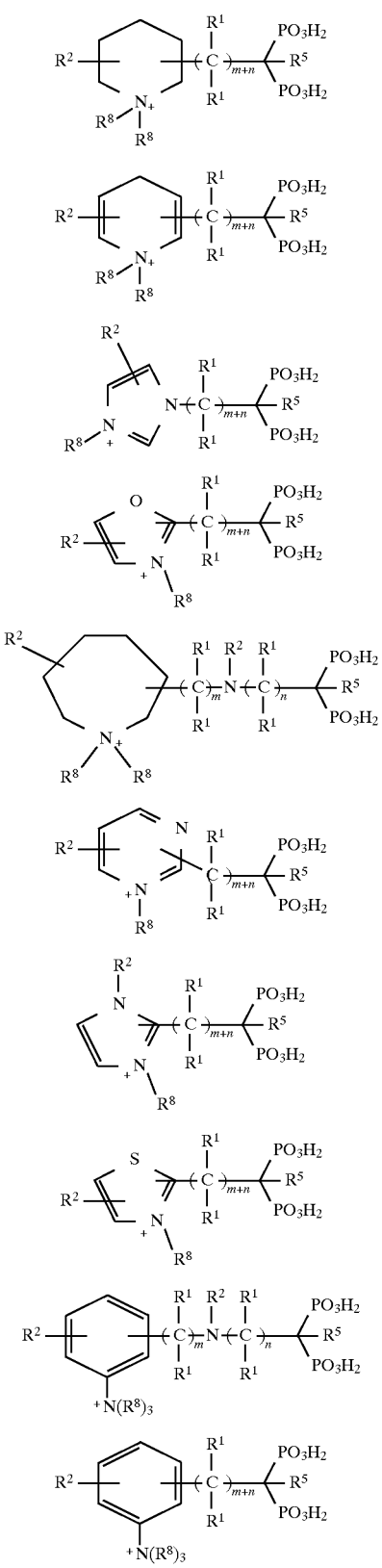

Specific examples of compounds of the present invention include:

2-(2-Hydroxy-2,2-diphosphonoethyl)-1,1-dimethylpiperidinium iodide Salt;
3-(2-hydroxy-2,2-diphosphonoethyl)-1-methylpyridinium iodide;
3-(2-hydroxy-2,2-diphosphonoethyl)-1-methylpyridinium hydroxide;
3-(2,2-diphosphonoethyl)-1-ethylpyridinium chloride;
3-(2,2-diphosphonoethyl)-1-(2-mercaptoethyl)pyridinium chloride;
2-(2-hydroxy-2,2-diphosphonoethyl)-1-methylpyridinium hydroxide;
3-(3-hydroxy-3,3-diphosphonopropyl)-1-methylpyridinium hydroxide;
3-(2,2-Diphosphono-2-hydroxyethyl)-1,1-dimethylpiperidinium iodide Salt;
3-(2,2-Diphosphonoethyl)-1-heptylpyridinium chloride;
3-(2,2-Diphosphonoethyl)-1-methylpyridinium chloride;
3-(2,2-Phosphonomethylphosphinoethyl)-1-methylpyridinium Iodide;
3-(2-Phosphono-2-sulfonoethyl)-1-methylpyridinium chloride;
3-(2-carboxy-2-phosphonoethyl)-1-methylpyridinium chloride;
2-diphosphonomethyl-1,1-dimethylpiperidinium chloride;
3-diphosphonomethyl-1,1-dimethylpiperidinium chloride;
4-diphosphonomethyl-1,1-dimethylpiperidinium chloride;
2-(2,2-diphosphonoethyl)-1,1-dimethylpiperidinium chloride;
3-(2,2-diphosphonoethyl)-1,1-dimethylpiperidinium chloride;
4-(2,2-diphosphonoethyl)-1,1-dimethylpiperidinium chloride;
2-(2,2-diphosphonoethyl)-1-methyl-1-(2-mercaptoethyl)piperidinium chloride;
3-(2,2-diphosphonoethyl)-1-methyl-1-(2-mercaptoethyl)piperidinium chloride;
4-(2,2-diphosphonoethyl)-1-methyl-1-(2-mercaptoethyl)piperidinium chloride;
2-[2,2-diphosphono-1-(2-mercaptoethyl)ethyl]-1,1-dimethylpiperidinium chloride;
3-[2,2-diphosphono-1-(3-mercaptopropyl)ethyl]-1,1-dimethylpiperidinium chloride;
4-[2,2-diphosphono-1-(2-acetylthioethyl)ethyl]-1,1-dimethylpiperidinium chloride;
2-(2,2-diphosphono-2-hydroxyethyl)-1,1-dimethylpiperidinium chloride;
3-(2,2-diphosphono-2-hydroxyethyl)-1,1-dimethylpiperidinium chloride;
4-(2,2-diphosphono-2-hydroxyethyl)-1,1-dimethylpiperidinium chloride;
2-(2,2-diphosphono-2-hydroxyethyl)-1,1,3-trimethylpiperidinium chloride;
2-(2,2-diphosphono-2-hydroxyethyl)-1,1,5-trimethylpiperidinium chloride;
2-(2,2-diphosphonoethyl)-1,1,3-trimethylpiperidinium chloride;
2-(2,2-diphosphonoethyl)-1,1,5-trimethylpiperidinium chloride;
2-(3,3-diphosphonopropyl)-1,1-dimethylpiperidinium chloride;
3-(3,3-diphosphonopropyl)-1,1-dimethylpiperidinium chloride;
4-(3,3-diphosphonopropyl)-1,1-dimethylpiperidinium chloride;
2-(3,3-diphosphono-3-hydroxypropyl)-1,1-dimethylpiperidinium chloride;
3-(3,3-diphosphono-3-hydroxypropyl)-1,1-dimethylpiperidinium chloride;
4-(3,3-diphosphono-3-hydroxypropyl)-1,1-dimethylpiperidinium chloride;

2-(2,2-diphosphonopropyl)-1,1-dimethylpiperidinium chloride;
3-(2,2-diphosphonopropyl)-1,1-dimethylpiperidinium chloride;
4-(2,2-diphosphonopropyl)-1,1-dimethylpiperidinium chloride;
2-(2,2-diphosphono-2-aminoethyl)-1,1-dimethylpiperidinium chloride;
3-(2,2-diphosphono-2-aminoethyl)-1,1-dimethylpiperidinium chloride;
4-(2,2-diphosphono-2-aminoethyl)-1,1-dimethylpiperidinium chloride;
2-(2,2-diphosphono-2-aminoethyl)-1,1,3-trimethylpiperidinium chloride;
2-(2,2-diphosphono-2-aminoethyl)-1,1,3-trimethylpiperidinium chloride;
3-(2,2-diphosphono-2-aminoethyl)-1,1,5-trimethylpiperidinium chloride;
2-(2,2-diphosphono-2-(methylamino)ethyl)-1,1,-dimethylpiperidinium chloride;
2-(4,4-diphosphono-4-hydroxybutyl)-1,1,3-trimethylpiperidinium chloride;
2-(4,4-diphosphono-4-hydroxybutyl)-1,1-dimethylpiperidinium chloride;
2-(2,2-diphosphono-2-hydroxyethyl)-3-carboxy-1,1-dimethylpiperidinium chloride;
2-(2,2-diphosphono-2-hydroxyethyl)-5-carboxy-1,1-dimethylpiperidinium chloride;
2-(2,2-diphosphonoethyl)-1-methylpyrimidinium chloride;
4-(2,2-diphosphonoethyl)-1-methylpyrimidinium chloride;
2-(2,2-diphosphono-2-hydroxyethyl)-1-methylpyrimidinium chloride;
4-(2,2-diphosphono-2-hydroxyethyl)-1-methylpyrimidinium chloride;
2-(3,3-diphosphonopropyl)-1-methylpyrimidinium chloride;
4-(3,3-diphosphonopropyl)-1-methylpyrimidinium chloride;
2-(3,3-diphosphono-1-hydroxypropyl)-1-methylpyrimidinium chloride;
4-(3,3-diphosphono-1-hydroxypropyl)-1-methylpyrimidinium chloride;
2-(2,2-diphosphono-2-aminoethyl)-1-methylpyrimidinium chloride;
3-[(diphosphonomethyl)oxo]-1,1-dimethylpiperidinium chloride;
4-[(diphosphonomethyl)oxo]-1,1-dimethylpiperidinium chloride;
3-[(2,2-diphosphonoethyl)oxo]-1,1-dimethylpiperidinium chloride;
4-[(2,2-diphosphonoethyl)oxo]-1,1-dimethylpiperidinium chloride;
3-[(diphosphonomethyl)thio]-1,1-dimethylpiperidinium chloride;
4-[(diphosphonomethyl)thio]-1,1-dimethylpiperidinium chloride; the pharmaceutically-acceptable salts and esters thereof.

Preferred compounds of the present invention include:
3-(2-hydroxy-2,2-diphosphonoethyl)-1-methylpyridinium iodide;
3-(2-hydroxy-2,2-diphosphonoethyl)-1-methylpyridinium hydroxide;
3-(2,2-diphosphonoethyl)-1-(2-mercaptoethyl)pyridinium chloride;
2-(2-Hydroxy-2,2-diphosphonoethyl)-1,1-dimethylpiperidinium iodide Salt;
3-(2,2-Diphosphono-2-hydroxyethyl)-1,1-dimethylpiperidinium iodide Salt;
3-(2,2-Diphosphonoethyl)-1-heptylpyridinium chloride;
3-(2,2-Diphosphonoethyl)-1-methylpyridinium chloride;
2-(2,2-diphosphonoethyl)-1,1-dimethylpiperidinium chloride;
3-(2,2-diphosphonoethyl)-1,1-dimethylpiperidinium chloride;
4-(2,2-diphosphonoethyl)-1,1-dimethylpiperidinium chloride;
2-(2,2-diphosphono-2-hydroxyethyl)-1,1-dimethylpiperidinium chloride;
3-(2,2-diphosphono-2-hydroxyethyl)-1,1-dimethylpiperidinium chloride;
4-(2,2-diphosphono-2-hydroxyethyl)-1,1-dimethylpiperidinium chloride;
2-(2,2-diphosphono-2-hydroxyethyl)-1,1,3-trimethylpiperidinium chloride;
2-(2,2-diphosphono-2-hydroxyethyl)-1,1,5-trimethylpiperidinium chloride;
2-[2,2-diphosphono-1-(2-mercaptoethyl)ethyl]-1,1-dimethylpiperidinium chloride;
3-[2,2-diphosphono-1-(3-mercaptopropyl)ethyl]-1,1-dimethylpiperidinium chloride;
2-(2,2-diphosphonoethyl)-1-methyl-1-(2-mercaptoethyl)piperidinium chloride;
3-(2,2-diphosphonoethyl)-1-methyl-1-(2-mercaptoethyl)piperidinium chloride;
4-(2,2-diphosphonoethyl)-1-methyl-1-(2-mercaptoethyl)piperidinium chloride;

Most preferred compounds of the present invention include:
3-(2-hydroxy-2,2-diphosphonoethyl)-1-methylpyridinium iodide;
3-(2-hydroxy-2,2-diphosphonoethyl)-1-methylpyridinium hydroxide;
3-(2,2-diphosphonoethyl)-1-(2-mercaptoethyl)pyridinium chloride;
2-[2,2-diphosphono-1-(2-mercaptoethyl)ethyl]-1,1-dimethylpiperidinium chloride;
3-[2,2-diphosphono-1-(3-mercaptopropyl)ethyl]-1,1-dimethylpiperidinium chloride;
2-(2,2-diphosphonoethyl)-1-methyl-1-(2-mercaptoethyl)piperidinium chloride;
3-(2,2-diphosphonoethyl)-1-methyl-1-(2-mercaptoethyl)piperidinium chloride;

In order to determine and assess pharmacological activity, testing of the phosphonate compounds in animals is carried out using various assays known to those skilled in the art. Thus, the in vivo bone antiresorptive activity may be conveniently demonstrated using an assay designed to test the ability of these compounds to inhibit the resorption of bone, which bone re-sorption is characteristic of abnormal calcium and phosphate metabolism. One such test known in the art is the Schenk model. Another useful art-known test is the adjuvant arthritis test. Also useful is the in vitro hydroxyapatite crystal growth inhibition test. These and other appropriate tests for pharmacological activity are disclosed and/or referred to in Shinoda et al., *Calcified Tissue International*, 35, pp 87–99 (1983); Schenk et al. , *Calcified Tissue Research*, 11, pp 196–214 (1973); Russell et al., *Calcified Tissue Research*, 6, pp 183–196 (1970); Muhlbauer and Fleisch, *Mineral Electrolyte Metab.* , 5 , pp 296–303 (1981); Nancollas et al., *Oral Biol.*, 15, 731 (1970); U.S. Pat. No. 3,683,080, to Francis, issued Aug. 8, 1972; U. S. Pat. No. 4,134,969, to Schmidt-Dunker, issued Jan. 16, 1979; and EPO Patent Application Publication No. 189,662, published Aug. 6, 1986; the disclosures of all these references being incorporated herein by reference in their entirety. Certain of these tests for pharmacological activity are also described in more detail in the Examples provided hereinafter.

In addition to being useful for treating or preventing pathological conditions characterized by abnormal calcium or phosphate metabolism, the compounds of the present invention may have other uses. For example, they may be useful in preventing the formation of tartar (i.e., calculus) and/or plaque on teeth. In addition, the compounds of the present invention are believed to be useful as bone scanning agents after labeling with 99m-technetium. In addition, the compounds of the present invention are useful as sequestering agents for polyvalent metal ions, particularly di- (e.g. calcium and magnesium) and trivalent (e.g. indium) metal ions. Thus, the compounds of the present invention are useful as builders in detergents and cleansers, or for treating water. They are also useful as stabilizers for compounds. Finally, the compounds of the present invention may be useful as herbicides which are non-toxic to animals.

The quaternary nitrogen-containing phosphonates to be included in the pharmaceutical compositions of the present invention can be made according to the following non-limiting Examples 1 to 16.

Compositions Containing Novel Quaternary Nitrogen-Containing-Phosphonate Compounds The novel quaternary nitrogen-containing phosphonate compounds of the present invention may be administered to humans or other mammals by a variety of routes, including, but not limited to, oral dosage forms and injections (intravenous, intramuscular, intraperitoneal and subcutaneous). Numerous other dosage forms containing the novel quaternary nitrogen-containing phosphonate compounds of the present invention can be readily formulated by one skilled in the art, utilizing the suitable pharmaceutical excipients as defined below. For considerations of patient compliance, oral dosage forms are generally most preferred.

The term "pharmaceutical composition" as used herein means a combination comprised of a safe and effective amount of the quaternary nitrogen-containing-phosphonate compound active ingredient, or mixtures thereof, and pharmaceutically-acceptable excipients.

The phrase "safe and effective amount", as used herein, means an amount of a compound or composition large enough to significantly positively modify the symptoms and/or condition to be treated, but small enough to avoid serious side effects (at a reasonable benefit/risk ratio), within the scope of sound medical judgment. The safe and effective amount of active ingredient for use in the pharmaceutical compositions to be used in the method of the invention herein will vary with the particular condition being treated, the age and physical condition of the patient being treated, the severity of the condition, the duration of the treatment, the nature of concurrent therapy, the particular active ingredient being employed, the particular pharmaceutically-acceptable excipients utilized, and like factors within the knowledge and expertise of the attending physician.

The term "pharmaceutically-acceptable excipients" as used herein includes any physiologically inert, pharmacologically inactive material known to one skilled in the art, which is compatible with the physical and chemical characteristics of the particular quaternary nitrogen-containing phosphonate compound active ingredient selected for use. Pharmaceutically-acceptable excipients include, but are not limited to, polymers, resins, plasticizers, fillers, binders, lubricants, glidants, disintegrants, solvents, co-solvents, buffer systems, surfactants, preservatives, sweetening agents, flavoring agents, pharmaceutical grade dyes or pigments, and viscosity agents.

The term "oral dosage form" as used herein means any pharmaceutical composition intended to be systemically administered to an individual by delivering said composition to the gastrointestinal tract of an individual, via the mouth of said individual. For purposes of the present invention, the delivered form can be in the form of a tablet, coated or non-coated; solution; suspension; or a capsule, coated or non-coated.

The term "injection" as used herein means any pharmaceutical composition intended to be-systemically administered to a human or other mammal, via delivery of a solution or emulsion containing the active ingredient, by puncturing the skin of said individual, in order to deliver said solution or emulsion to the circulatory system of the individual either by intravenous, intramuscular, intraperitoneal or subcutaneous injection.

The rate of systemic delivery can be satisfactorily controlled by one skilled in the art, by manipulating any one or more of the following:

(a) the active ingredient proper;

(b) the pharmaceutically-acceptable excipients; so long as the variants do not interfere in the activity of the particular active ingredient selected;

(c) the type of the excipient, and the concomitant desirable thickness and permeability (swelling properties) of said excipients;

(d) the time-dependent conditions of the excipient itself and/or within the excipients;

(e) the particle size of the granulated active ingredient; and (f) the pH-dependent conditions of the excipients.

In particular, the solubility, acidity, and susceptibility to hydrolysis of the different quaternary nitrogen-containing phosphonate active ingredients, such as acid addition salts, salts formed with the carboxylic group, e.g., alkali metal salts, alkaline earth metal salts, etc., and esters, e.g., alkyl, aryl, aralkyl, may be used as guidelines for the proper choice. In addition, suitable pH-conditions might be established within the oral dosage forms by adding a suitable buffer to the active ingredient in accordance with the desired release pattern.

Dosage forms particularly suitable for administering anti-calculus and antiplaque compositions of the present invention are: Dentifrices (including toothpastes and tooth powders), mouthwashes and spray, dental solutions, oral gels and chewing gum. Preferred compositions of the subject invention are in the form of dentifrices. Components of toothpastes generally include a dental abrasive (from 10% to 50%), a surfactant (from 0.5% to 10%), a thickening agent (from 0.1% to 5%), a humectant (from 10% to 55%), a flavoring agent (from 0.04% to 2%), a sweetening agent (from 0.1% to 3%), a coloring agent (from 0.01% to 0.5%) and water (from 2% to 45%). Dentifrices may also include a safe and effective amount of a fluoride ion source, which typically is in the form of a water-soluble fluoride compound. This water-soluble fluoride compound is typically present in the compositions of the subject invention in an amount sufficient to give a fluoride concentration of from 0.005% to 2.0% by weight. Preferred fluoride sources are sodium fluoride, acidulated phosphate fluoride, and sodium monofluorophosphate. U.S. Pat. No. 3,678,154, issued Jul. 18, 1972 to Widder et al., discloses such salts as well as others, and is incorporated herein by reference.

Other preferred compositions of the subject invention are mouthwashes and mouth sprays. Components of such mouthwashes and mouth sprays include water (from 45% to 95%), ethanol (from 0% to 25%), humectant (from 0% to 50%), surfactant agent (from 0.01% to 7%), flavoring agent (from 0.04% to 2%), sweetening agent (from 0.1% to 3%), and coloring agent (from 0.001% to 0.5%). Such mouthwashes and mouth sprays may also include one or more of an anticalculus agent (from 0.15 to 3%), and an antiplaque agent (from 0.1% to 5%).

Other preferred compositions of the subject invention are dental solutions. Components of such dental solutions generally include water (from about 90% to about 99%), preservative (from 0.01% to 0.5%), thickening agent (from 0% to 5%), flavoring agent (from 0.04% to 2%), sweetening agent (from 0.1% to 3%), and surfactant (from 0% to 5%).

Oral gel compositions typically include one or more of water (from 0% to 99%), a humectant such as glycerin (from 0% to 99%), a thickening agent (from 0.1% to 5%), a flavoring agent (from 0.04% to 2%), and a sweetening agent (from 0.01% to 0.5%).

Chewing gum compositions typically include one or more of a gum base (from 50% to 90%), a flavoring agent (from 0.04% to 2%) and a sweetening agent (from 0.01% to 20%).

As stated hereinabove, pharmaceutically-acceptable excipients include, but are not limited to, resins, fillers, binders, lubricants, solvents, glidants, disintegrants co-solvents, surfactants, preservatives, sweetener agents, flavoring agents, buffer systems, pharmaceutical-grade dyes or pigments, and viscosity agents.

The preferred solvent is water.

Flavoring agents among those useful herein include those described in *Remington's Pharmaceutical Sciences*, 18th Edition, Mack Publishing Company, 1990, pp. 1288–1300, incorporated by reference herein. The pharmaceutical compositions suitable for use herein generally contain from 0 to 2% flavoring agents.

Particularly preferred flavoring agents for compounds of the present invention useful in treating or preventing dental calculus and plaque are menthol, oil of wintergreen, oil of peppermint, oil of spearmint or oil of clove. Flavoring agents are generally included in anticalculus and antiplaque compositions in amounts of from 0% to 3%, preferably from 0.04% to 2% by weight.

Dyes or pigments among those useful herein include those described in *Handbook of Pharmaceutical Excipients*, pp. 81–90, 1986 by the American Pharmaceutical Association & the Pharmaceutical Society of Great Britain, incorporated by reference herein. The pharmaceutical compositions herein generally contain from 0–2% dyes or pigments.

Preferred co-solvents include, but are not limited to, ethanol, glycerin, propylene glycol, polyethylene glycols. The pharmaceutical compositions of the present invention include from 0–50% co-solvents.

Preferred buffer systems include, but are not limited to, acetic, boric, carbonic, phosphoric, succinic, malaic, tartaric, citric, acetic, benzoic, lactic, glyceric, gluconic, glutaric and glutamic acids and their sodium, potassium and ammonium salts. Particularly preferred are phosphoric, tartaric, citric, and acetic acids and salts. The pharmaceutical composition of the present invention generally contain from 0–5% buffer systems.

Preferred surfactants include, but are not limited to, polyoxyethylene sorbitan fatty acid esters, polyoxyethylene monoalkyl ethers, sucrose monoesters and lanolin esters and ethers, alkyl sulfate salts, sodium, potassium, and ammonium salts of fatty acids. The pharmaceutical compositions of the present invention include 0–2% surfactants. Preferred surfactants for compounds of present invention useful in treating or preventing dental calculus and plaque include those surfactants which are reasonably stable and foam throughout a wide pH range, including nonsoap anionic, nonionic, zwitterionic and amphoteric organic synthetic detergents. Many suitable surfactants are disclosed in U.S. Pat. No. 4,051,234, issued Sep. 27, 1977, to Gieske et al., and in U.S. Pat. No. 3,959,458 issued to Agricola, Briner, Granger & Widder on May 25, 1976, both of which are incorporated herein by reference. Such surfactants are generally present in the compositions of the subject invention at a level of from 0% to 10%, preferably from 0.2% to 5%. Surfactants may also be used as solubilizing agents to help retain sparingly soluble components, e.g., some flavoring agents, in solution. Surfactants suitable for this purpose include polysorbates and polyoxamers.

Preferred preservatives include, but are not limited to, phenol, alkyl esters of parahydroxybenzoic acid, o-phenylphenol benzoic acid and the salts thereof, boric acid and the salts thereof, sorbic acid and the salts thereof, chlorobutanol, benzyl alcohol, thimerosal, phenylmercuric acetate and nitrate, nitromersol, benzalkonium chloride, cetylpyridinium chloride, methyl paraben, and propyl paraben. Particularly preferred are the salts of benzoic acid, cetylpyridinium chloride, methyl paraben and propyl paraben. The compositions of the present invention generally include from 0–2% preservatives.

Preferred sweeteners include, but are not limited to, sucrose, glucose, saccharin, sorbitol, mannitol, and aspartame. Particularly preferred are sucrose and saccharin. Pharmaceutical compositions of the present invention include 0–5% sweeteners.

Preferred viscosity agents include, but are not limited to, methylcellulose, sodium carboxymethylcellulose, hydroxypropylmethylcellulose, hydroxypropylcellulose, sodium alginate, carbomer, povidone, acacia, guar gum, xanthan gum and tragacanth. Particularly preferred are methylcellulose, carbomer, xanthan gum, guar gum, povidone, sodium carboxymethylcellulose, and magnesium aluminum silicate. Compositions of the present invention include 0–5% viscosity agents.

Preferred fillers include, but are not limited to, lactose, mannitol, sorbitol, tribasic calcium phosphate, dibasic calcium phosphate, compressible sugar, starch, calcium sulfate, dextro and microcrystalline cellulose. The compositions of the present invention contain from 0–75% fillers.

Preferred lubricants include, but are not limited to, magnesium stearate, stearic acid, and talc. The pharmaceutical compositions of the present invention include 0.5–2% lubricants.

Preferred glidants include, but are not limited to, talc and colloidal silicon dioxide. The compositions of the present invention include from 1–5% glidants.

Preferred disintegrants include, but are not limited to, starch, sodium starch glycolate, crospovidone, croscarmelose sodium, and microcrystalline cellulose. The pharmaceutical compositions of the present invention include from 4–15% disintegrants.

Preferred binders include, but are not limited to, acacia, tragacanth, hydroxypropylcellulose, pregelatinized starch, gelatin, povidone, hydroxypropylcellulose, hydroxypropylmethylcellulose, methylcellulose, sugar solutions, such as sucrose and sorbitol, and ethylcellulose. The compositions of the present invention include 1–10% binders.

In preparing oral compositions, useful in treating and preventing dental plaque and calculus, it is desirable to add binders and/or thickening agents, particularly to toothpaste compositions. Preferred binders and thickening agents include for example, carboxyvinyl polymers, polysaccharide gums such as xanthan gum, carrageenan, hydroxyethyl cellulose and water soluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate or finely divided silica can be used as part of the thickening agent to further improve texture. These binders and thickening agents are generally present in amounts from 6%, preferably from 0.1% to 5% by weight.

Another optional component useful in preparing oral compositions is a humectant. The humectant serves to keep toothpaste compositions from hardening upon exposure to air, and to give mouthwash and toothpaste compositions a moist feel to the mouth. Certain humectants can also impart desirable sweetness of flavor to mouthwash and toothpaste compositions. The humectant, on a pure humectant basis, generally comprises from 0% to 70%, preferably from 2% to 55%, by weight of the compositions herein. Suitable humectants include edible polyhydric alcohols such as glycerin, sorbitol, xylitol, polyethylene glycol, and propylene glycol, especially sorbitol and glycerin.

Opacifiers may also be used in toothpastes of the subject invention to render the toothpaste opaque. Suitable opacifiers include titanium dioxide and some abrasives including, for example, magnesium aluminum silicate.

Preferred dental abrasives useful in formulating dentifrices include, for example, silicas including gels and precipitates, calcium carbonate, dicalcium orthophosphate dehydrate, calcium pyrophosphate, tricalcium phosphate, calcium polymetaphosphate, insoluble sodium polymetaphosphate, hydrate alumina, and resinous abrasive materials such as particulate condensation products of urea and formaldehyde, and other materials such as those disclosed by Cooley et al. in U.S. Pat. No. 3,070,510, issued Dec. 25, 1962, hereby incorporated herein by reference. Mixtures of abrasives may also be used.

Silica dental abrasives, of various types, can provide the unique benefits of exceptional dental cleaning and polishing performance without unduly abrading tooth enamel or dentin. Accordingly, they are preferred for use herein.

The silica abrasive polishing materials useful herein, as well as the other abrasives, generally have an average particle size ranging between about 0.1 to 30 microns, preferably between 5 and 15 microns. The silica abrasive can be precipitated silica or silica gels such as the silica xerogels described in U.S. Pat. No. 3,538,230, issued Mar. 2, 1970 to Pader et al., and in U.S. Pat. No. 3,862,307, issued Jun. 21, 1975 to DiGiulio, both incorporated herein by reference. Preferred are the silica xerogels marketed under the tradename Syloid® by the W.R. Grace & Company, Davidson Chemical Division. Preferred precipitated silica materials include those marketed by the J. M. Huber Corporation under the Tradename, Zeodent®, particularly the silica carrying the designation Zeodent® 119. These silica abrasives are described in U.S. Pat. No. 4,340,583, Wason, issued Jul. 20, 1982, incorporated herein by reference.

Mixtures of abrasives may be used. The amount of abrasive in the compositions described herein ranges from about 6% to about 70%, preferably from 15% to 50%, when the dentifrice is a toothpaste. Higher levels, as high as 90%, may be used if the composition is a tooth powder.

Compounds of the present invention may comprise from 0.1% to 99.9% by weight of the pharmaceutical compositions of the present invention. Preferably the compounds of the present invention comprise from about 20% to about 80% by weight of the pharmaceutical compositions useful in treating or preventing osteoporosis and arthritis, including rheumatoid arthritis and osteoarthritis.

Accordingly, the pharmaceutical compositions of the present invention useful in treating or preventing osteoporosis, and arthritis, including rheumatoid arthritis and osteoarthritis, include from 15–95% of a quaternary nitrogen-containing phosphonate compound active ingredient, or mixture, thereof; 0–2% flavoring agents; 0–50% co-solvents; 0–5% buffer system; 0–2% surfactants; 0–2% preservatives; 0–5% sweeteners; 0–5% viscosity agents; 0–75% fillers; 0.5–2% lubricants; 1–5% glidants; 4–15% disintegrants; and 1–10% binders.

Compositions of the present invention specifically for the treatment or prevention of dental calculus and plaque preferably comprise aqueous solutions of the compounds of the present invention. Such compositions typically comprise from 0.5% to 10% by weight, preferably from 0.1% to 5% by weight, and most preferably from 0.5% to 3% by weight of a compound of the present invention. For a mouth rinse formulation, the most preferred concentration of a compound of the present invention ranges from about 1% to about 2% by weight.

Suitable pharmaceutical compositions are described herein in Examples 19 to 21. Suitable dental compositions are described herein in Examples 22 to 23. It is well within the capabilities of one skilled in the art to vary the non-limiting examples described herein to achieve a broad range of pharmaceutical compositions.

The choice of a pharmaceutical excipient to be used in conjunction with the quaternized nitrogen-containing phosphonate compounds of the present compositions is basically determined by the way the phosphonate is to be administered. If the compound is to be injected, the preferred pharmaceutical carrier is sterile, physiological saline, the pH of which has been adjusted to about 7.4. However, the preferred mode of administering the phosphonates of the present invention is orally, and the preferred unit dosage form is therefore tablets, capsules and the like, comprising from about 0.1 mg P to about 600 mg P of the phosphonic acid compounds described herein. Pharmaceutical carriers suitable for the preparation of unit dosage forms for oral administration are well known in the art. Their selection will depend on secondary considerations like taste, cost, and shelf stability, which are not critical for the purposes of the present Invention, and can be made without difficulty by a person skilled in the art.

The term "mg P", as used herein, means the weight of the phosphorus atoms present in an amount of a phosphonic acid compound of the present invention. This unit is used to standardize the amount of the phosphonic acid compounds of the present invention to be used in the pharmaceutical compositions and methods of the present inventions. For example, 3-(2,2-diphosphonoethyl)-1-(2-mercaptoethyl) pyridinium chloride has a molecular weight of 363.7 g/mole, of which 17% ( 62 g/mole) is due to the two phosphorus atoms present in this molecule. One milligram of this compound is therefore calculated to have 0.17 mg P. Thus, to prepare a pharmaceutical composition containing 0.17 mg P of this compound, the composition should contain 1 mg of the compound; and to dose 0.17 mg P/kg of this compound to a 50 kg patient, the patient would be dosed with 50 mg of this compound.

The pharmaceutically-acceptable excipient employed in conjunction with the phosphonates of the present invention is used at a concentration sufficient to provide a practical size to dosage relationship. Preferably, the pharmaceutically-acceptable carriers, in total, may comprise from 0.1% to 99.9% by weight of the total composition and more preferably from 20% to 80%.

Method for Treating or Preventing Diseases Characterized by Abnormal Calcium and Phosphate Metabolism Another aspect of the present invention is methods for treating or preventing diseases characterized by abnormal calcium and phosphate metabolism. Additionally, the present invention relates to a method of treating and preventing dental calculus and plaque. Such methods comprise administering to a human or other mammal in need of such treatment a safe and effective amount of phosphonate compound of the present invention.

The preferred mode of administration is oral, but other known methods of administration are contemplated as well, e.g., dermatomucosally (for example, dermally, rectally and the like) and parenterally (for example, by subcutaneous injection, intramuscular injection, intra-articular injection, intravenous injection and the like). Inhalation is also included. Thus, specific modes of administration include, without limitation, oral, transdermal, mucosal, sublingual, intramuscular, intravenous, intraperitoneal, and subcutaneous administration, as well as topical application.

The term "abnormal calcium and phosphate metabolism", as used herein, means (1) conditions which are characterized by anomalous mobilization of calcium and phosphate leading to general or specific bone loss, or excessively high calcium and phosphate levels in the fluids of the body; and (2) conditions which cause or result from deposition of calcium and phosphate anomalously in the body. The first category includes, but is not limited to, osteoporosis, Paget's disease, hyperparathyroidism, hypercalcemia of malignancy, heterotopic ossification, and osteolytic bone metastases. The second category includes, but is not limited to, myositis ossificans progressiva, calcinosis universalis, and such afflictions as arthritis, (including rheumatoid arthritis and osteoarthritis) neuritis, bursitis, tendonitis and other inflammatory conditions which predispose involved tissue to deposition of calcium and phosphate.

The term "rheumatoid arthritis" as used herein, means a chronic systemic and articular inflammatory disorder of unknown etiology. It is characterized by destruction of articular cartilage, ligaments, tendons, and bone.

The term "osteoarthritis" as used herein, means a non-inflammatory disorder of the movable joints. It is characterized by deterioration and abrasion of the articular cartilage, and new bone formation at the joint surface.

The terms "person at risk" and "person in need of such treatment", as used herein, mean any human or other mammal which suffers a significant risk of abnormal calcium and phosphate metabolism if left untreated, and any human or other mammal diagnosed as being afflicted with abnormal calcium and phosphate metabolism. For example, postmenopausal women; persons undergoing certain steroid therapy; persons on certain anti-convulsant drugs; persons diagnosed as having Paget's disease, hyperparathyroidism, hypercalcemia of malignancy, or osteolytic bone metastases; persons diagnosed as suffering from one or more of the various forms of osteoporosis; persons belonging to a population group known to have a significantly higher than average chance of developing osteoporosis, e.g., postmenopausal women, men over age 65, and persons being treated with drugs known to cause osteoporosis as a side effect; persons diagnosed as suffering from myositis ossificans progressiva or calcinosis universalis; and persons afflicted with arthritis, osteoarthritis, rheumatoid arthritis, neuritis, bursitis, tendonitis and other conditions which predispose involved tissue to deposition of calcium and phosphate.

The phrase "safe and effective amount", as used herein, means an amount of a compound or composition of the present invention high enough to significantly positively modify the condition to be treated, but low enough to avoid serious side effects (at a reasonable benefit/risk ratio), within the scope of sound medical judgment. The safe and effective amount of phosphonate compounds of the present invention will vary with the particular condition being treated, the age and physical condition of the patient being treated, the severity of the condition, the duration of the treatment, the nature of concurrent therapy, the specific phosphonate employed, the particular pharmaceutically-acceptable carrier utilized, and like factors within the knowledge and expertise of the attending physician. Single dosages, for the methods of treatment for abnormal calcium and phosphate metabolism, can range from 0.01 mg P to 3500 mg P, or from 0.0002 to 70 mg P/kg of body weight (based on a body weight of 50 kg). Preferred single dosages are from 1 mg P to 600 mg P, or from 0.02 to 12 g P/kg of body weight (based on a body weight of 50 kg). Up to about four single dosages per day may be administered. Daily dosages greater than 500 mg P/kg are not required to produce the desired effect and may produce undesirable side effects. The higher dosages within this range are, of course, required in the case of oral administration because of limited absorption.

Dosing of the compounds of the present invention useful in treating or preventing dental calculus and plaque include dentifrices such as toothpaste and tooth powders containing 0.05%–10% by weight of a compound of the present invention, and dental solutions such as mouthwashes containing 0.05–5% by weight of a compound of the present invention.

The following Examples further describe and demonstrate the preferred embodiments within the scope of the present invention. The Examples are given solely for the purpose of illustration, and are not to be construed as limitations of the present invention since many variations thereof are possible without departing from its spirit and scope.

EXAMPLE 1

Synthesis of 3-(2,2-Pyiphosphonoethyl)-1-ethylpyridinium Chloride

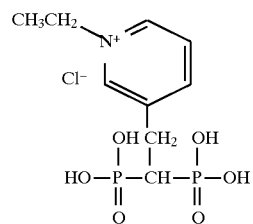

I. Synthesis of 2-[3-Pyridinylethylidene]bis[phosphonic acid] tetraethyl ester

To a mixture of 60% sodium hydride in mineral oil (4.00 g, 0.10 mmol) in DMSO (155 ml) is added tetraethylmethylenediphosphonate (30 g, 0.10 mmol) in DMSO (20 ml) at 0° C. The reaction mixture is stirred at 0° C. for 30 minutes then at room temperature for 30 minutes. This mixture is then added dropwise via an addition funnel to 3-picolyl chloride (0.11 mmol) in DMSO (100 ml) at room temperature. The reaction is allowed to stir for an additional 12 hours at room temperature, the reaction is then quenched by the addition of saturated aqueous ammonium chloride. Said reaction mixture is extracted with methylene chloride and the organic extracts are combined, dried over sodium sulfate, filtered and concentrated under reduced pressure. The product is purified by flash chromatography with 5% isopropanol in methylene chloride on silica gel.

II. Synthesis of Tetraethyl-3-(2,2-diphosphonoethyl)-1-ethyl pyridinium

To a solution of tetra ethyl 2-(3-pyridinyl)ethylidene-1,1-bisphosphonate tetraethyl ester (1.96 g, 5.17 mmol) in acetone (10 ml) is added iodoethane (4.03 g, 25.86 mmol). The reaction is heated at reflux under an atmosphere of nitrogen for 24 hours. The reaction mixture is concentrated under reduced pressure and the crude residue is triturated with hexanes and then with diethyl ether. In this way the N-ethyl pyridinium adduct is obtained as a hygroscopic orange solid (2.28 g) in an 83% yield.

III. Synthesis of 3-(2,2-Diphosphonoethyl)-1-ethylpyridinium chloride

The phosphonate esters are hydrolyzed by refluxing (2.18 g, 4.08 mmol) in 6N HCl (30 ml) for 12 hours under an atmosphere of nitrogen. The reaction mixture is cooled and then concentrated under reduced pressure. The product is obtained cleanly by triturating with diethyl ether.

EXAMPLE 2

Synthesis of 3-(2.2-Diphosphonoethyl)-1-(2-mercaptoethyl-)pyridinium Chloride

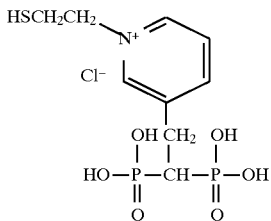

I. Synthesis of tetraethyl-3-(2.2 diphosphonoethyl)-1-(2-acetyl thio ethyl) pyridinium bromide To a solution of tetra ethyl 2-[3-pyridinyl)ethylidene]-1,1-bis[phosphonic acid] tetraethyl ester, prepared as described in Example 1 (Part I) hereinbefore, (3.16 g, 8.35 mmol) in acetone (20 ml) is added S-acetyl-2-bromoethanethiol (3.82 g, 20.88 mmol). The reaction is heated at reflux for 24 hours under an atmosphere of nitrogen. The reaction mixture is concentrated under reduced pressure and the crude residue is triturated with hexanes and then with diethyl ether. The residue is further purified by flash chromatography on silica gel with 20% methanol in methylene chloride. In this way the quaternized adduct is obtained as a pale yellow oil (1.69 g).

II. Synthesis of 3-(2,2-diphosphonoethyl)-1-(2-mercaptoethyl) pyridinium chloride The phosphonate esters are hydrolyzed by refluxing (1.45 g, 5.10 mmol) in 6N HCl (35 ml) for 20 hours under an atmosphere of nitrogen. The reaction mixture is cooled and concentrated. The product can be obtained cleanly by triturating with diethyl ether.

EXAMPLE 3

Synthesis of 3-(2-Hydroxy-2,2-diphosphonoethyl)-1-methylyyridinium Iodide Disodium Salt

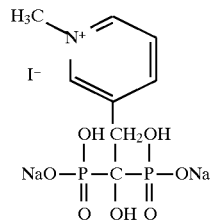

I. Synthesis of rl-Hydroxy-2-(3-pyridinyl)ethylidenel-bis [phosphonic acid]

To a 250 ml 3-neck round bottom flask equipped with a condenser and a dropping funnel is added 3-pyridylacetic acid hydrochloride (1.74 g, 10 mmole), phosphorous acid (2.46 g, 30 mmole) and 50 ml chlorobenzene. The flask is placed in a boiling water bath and phosphorus trichloride (4.0 g, 30 mmole) is added dropwise from the dropping funnel to the reaction mixture. This is stirred for 3 hours at 100° C. and a yellow, gummy oil forms during the course of this reaction. After 3 hours, the reaction mixture is cooled in an ice bath and the excess chlorobenzene is decanted. The oil is hydrolyzed in 100 ml of IN HCl overnight, cooled, and the first crop of crystals is filtered and washed with ethanol. The filtrate is evaporated to an oil and a small amount of water is added to dissolve the oil. Ethanol is added to induce crystallization. The second crop of crystals is filtered and washed with ethanol and combined with the first crop to yield 2.1 g after recrystallizing from hot water.

II. Synthesis of 3-(2-Hydroxy-2,2-diphosphonoethyl)-1-methyl pyridinium Iodide Disodium Salt To a solution of [1-hydroxy-2-(3-pyridinyl)ethylidene]bis [phosphonic acid] (0.5 g, 1.77 mmol) in 4.4 ml of 1N NaOH is added 14 ml of distilled water. To this is added methyl iodide in ethanol (12 ml) (1.25 g, 8.83 mmol). The pH of the reaction mixture is 6.0. The mixture is heated overnight at 80° C. The solvents are evaporated and the residue is triturated with acetone. The product is recrystallized from water and ethanol to yield 3-(2-hydroxy-2,2-diphosphonoethyl)-1-methyl pyridinium iodide disodium salt.

EXAMPLE 4

Synthesis of 3-(2-Hydroxy-2.2-diphosphonoethyl)-1-methylpyridinium Hydroxide, Inner Salt

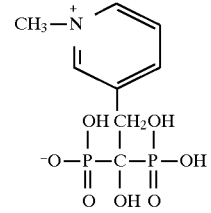

3-(2-Hydroxy-2,2-diphosphonoethyl)-1-methyl pyridinium iodide disodium salt, prepared as described in Example 3 hereinbefore, (0.42 9 0.89 mmol) in 6N HCl (40 ml) is heated at reflux for 12 hours. The reaction mixture is cooled and then washed with chloroform (5×40 ml) to remove iodine. The aqueous layer is concentrated under reduced pressure. The crude residue is triturated with acetone to provide the desired inner salt (255 mg) as a pale yellow solid in an 85% yield.

EXAMPLE 5

2-(2-Hydroxy-2,2-diphosphonoethyl)-1-methylpyridinium Hydroxide, Inner Salt, Monosodium Salt

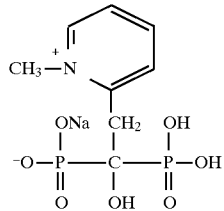

I. Synthesis of [1-Hydroxy-2-(2-pyridinyl)ethylidene]-bis[phosphonic acid]

To a 250 ml 3-neck round bottom flask equipped with a condenser and a dropping funnel is added 2-pyridylacetic acid hydrochloride (1.74 g, 10 mmole), phosphorous acid (2.46 g, 30 mmole) and 50 ml chlorobenzene. The flask is placed in a boiling water bath and phosphorus trichloride (4.08 g, 30 mmole) is added dropwise from the dropping funnel to the reaction mixture. This is stirred for 3 hours at 100° C. and a yellow, gummy oil forms during the course of the reaction. After 3 hours, the reaction mixture is cooled in an ice bath and the excess chlorobenzene is decanted. 100 ml of water is added to the oil and this mixture is refluxed overnight. After refluxing, the mixture is cooled and some product begins precipitating out. This precipitate is filtered and washed with ethanol to obtain the first crop of crystals. To get a second crop of crystals, the filtrate is evaporated down to an oil and a small amount of water is added to the oil until it is dissolved. Ethanol is added to induce crystallization. The second crop of crystals is filtered and washed with ethanol and combined with the first crop to give a total yield of 1.87 g after recrystallizing from hot water.

II. Synthesis of 2-(2-hydroxy-2,2-diphosphonoethyl)-1-methyl Pyridinium Hydroxide, Inner Salt, Monosodium Salt

[1-Hydroxy-2-(2-pyridinyl)ethylidene]bis[phosphonic acid] (3.53 mmol, 1.0 g) is dissolved in 8.8 ml of 1N sodium hydroxide solution and 8.8 ml of distilled water. To this is added iodomethane (17.67 mmol, 1.1 ml) in 18 ml of ethanol. This reaction mixture is heated at 80° C. until complete. The solvent is concentrated in vacuo and the residue is recrystallized from ethanol and water to yield 0.92 g of 2-($^2$-hydroxy-2,2-diphosphonoethyl)-1-methyl pyridinium hydroxide, inner salt, monosodium salt.

EXAMPLE 6

3-(3-Hydroxy-3,3-diphosphonoproyl)-1-methylpyridinium Hydroxide, Inner Salt

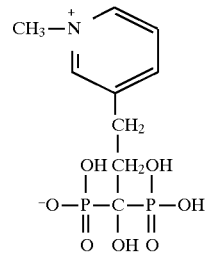

I. Synthesis of 3-(3-pyridinyl)propanoic acid

β-(3-Pyridyl)-acrylic acid (10 g) is placed in a Parr hydrogenation bottle with 150 ml of glacial acetic acid, 100 ml of absolute ethanol and a large scoop of palladium on carbon catalyst. The solution is shaken at 50 psi of hydrogen and re-pressurized as needed until hydrogen uptake ceases (approximately 3 hours). The solution is filtered through celite, washed with ethanol and the solvent is evaporated in vacuo and azeotroped with toluene to yield the desired product as white crystals.

II. Synthesis of [1-Hydroxy-3-(3-pyridinyl)propylidene]-bis[phosphonic acid]

To a 250 ml 3-neck round bottom flask equipped with a condensor and dropping funnel is added 3-pyridylpropionic acid (12.03 g, 79.6 mmol), phosphorous acid (19.6 g, 239 mmol) and 50 ml of chlorobenzene. The flask is placed in a 100° C. bath and phosphorus trichloride (20.88 ml, 239 mmol) is added dropwise to the reaction mixture. The reaction is stirred for 3 hours forming a gummy oil at which time the chlorobenzene is decanted and 100 ml of 1N HCl is added and the mixture is refluxed overnight at 100° C. The solution is cooled and the white precipitate which forms is filtered and washed with ethanol and ether to yield 16.9 g of the desired product.

III. Synthesis of 3-(3-hydroxy-3,3-diphosphonopropyl)-1-methyl pyridinium hydroxide, inner salt

[1-Hydroxy-3-(3-pyridinyl)propylidene]bis[phosphonic acid](3.37 mmol, 1.0 g) is dissolved in 8.4 ml of 1N NaOH solution with 29 ml of distilled water. Iodomethane (16.83 mmol, 1.05 ml) is added in 19 ml of ethanol. This reaction mixture is heated at 80° C. overnight. The solvent is evaporated in vacuo and the residue is triturated with acetone then recrystallized from ethanol and water to yield 0.5 g of 3-(3-hydroxy-3,3-diphosphono-propyl)-1-methyl pyridinium hydroxide, inner salt.

EXAMPLE 7

Synthesis of 3-(2,2-diphosphonoethyl)-1-heptylpyridinium Chloride

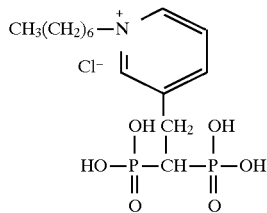

The above compound is prepared and synthesized as described hereinbelow.

I. Synthesis of Tetraethyl-3-(2.2-diphosphonoethyl)-1-heptylpyridinium iodide

A solution of 2-[(3-pyridinyl)ethylidene]bis[phosphonic acid] tetra ethyl ester (4.0 g, 10.5 mmol), prepared as described in Example 1 (Part I) hereinbefore, and 1-iodoheptane (7.14 g, 31.6 mmol) in dry acetonitrile (25 ml) is heated at reflux for 72 hours under nitrogen. The reaction mixture is evaporated in vacuo to dryness. The residue is triturated two times in diethyl ether, filtered and dried in a vacuum desiccator to provide the N-heptyl adduct (6.37 g).

II. Synthesis of 3-(2.2-Diphosphonoethyl)-1-heptylpyridinium Chloride

The N-heptyl adduct (6.20 g, 10.2 mmol) is heated at reflux in 6N hydrochloric acid (62 ml) for 48 hours. The reaction mixture is evaporated in vacuo to dryness, acetone is added and the mixture is evaporated to dryness a second time. The residue is triturated in ethanol to give a yellow solid which was collected by filtration, washed with diethyl ether and dried in a vacuum desiccator to yield 29% (for two steps) of the N-heptyl pyridinium bisphosphonic acid (1.19 g).

EXAMPLE 8

Synthesis of 3-(2,2-Diphosphonoethyl)-1-methylpyridinium chloride $$\text{CH}_3-\overset{+}{\text{N}} \quad \text{Cl}^- \quad \text{pyridinyl ring with } -\text{CH(OH)}\text{CH}_2\text{ substituent; HO}-\overset{\text{OH}}{\underset{\text{O}}{\text{P}}}-\text{CH}-\overset{\text{OH}}{\underset{\text{O}}{\text{P}}}-\text{OH}$$

The above compound is prepared and synthesized as described hereinbelow.

I. Synthesis of Tetraethyl-3-(2.2-diphosphonoethyl)-1-methylpyridinium iodide

A solution containing 2-[(3-pyridinyl)ethylidene]bis[phosphonic acid] tetra ethyl ester (5.0 g, 13.2 mmol), prepared as described in Example 1, Part I, hereinbefore, iodomethane (5.60 g, 39.5 mmol) and dry acetonitrile (32 ml) is heated at reflux for 72 hours. The reaction mixture is evaporated in vacuo to dryness, acetone is added and the mixture is evaporated to dryness a second time. The crude product is triturated in hexanes/diethyl ether, collected by filtration under nitrogen and dried in a vacuum desiccator to yield 5.0 g of the N-methyl pyridinium adduct.

II. Synthesis of 3-(2,2-Diphosphonoethyl)-1-methylpyridinium chloride

The phosphonate esters are hydrolyzed by refluxing the N-methylated adduct (5.0 g, 13.1 mmol) in 6N hydrochloric acid (54 ml) for 48 hours. The reaction mixture is evaporated in vacuo to dryness, acetone is added and the mixture evaporated in vacuo to dryness a second time. The residue is triturated in ethanol to give a solid which is collected by filtration. The crude product is dissolved in a minimum amount of water and treated with charcoal then filtered through celite. The filtrate is poured into ethanol to precipitate the product which is collected by filtration and dried in a vacuum desiccator to provide the N-methylated bisphosphonic acid (1.05 g, 25% yield for two steps).

EXAMPLE 9

Synthesis of 3-(2-Phosphono-2-methylphosphinoethyl)-1-methyl-pyridinium Iodide $$\text{H}_3\text{C}-\overset{+}{\text{N}} \quad \text{Cl}^- \quad \text{HO}-\overset{\text{OH}}{\underset{\text{O}}{\text{P}}}-\text{CH}-\overset{\text{OH}}{\underset{\text{O}}{\text{P}}}-\text{CH}_3$$

The above compound is prepared and synthesized as described hereinbelow.

I. Synthesis of 2-(3-Pyridinylethylidene)phosphonomethylphosphinic acid triethyl ester Using essentially the same procedure as described in Example 1, Part I hereinbefore, methylene phosphonomethylphosphinate triethyl ester [prepared as described by Henning, H. G. and Petzold, G. in Z. Chem., Vol. 5, pp. 419 (1965)] is converted to 2-(3-Pyridinylethylidene) phosphonomethylphosphinic acid triethyl ester.

II. Synthesis of Triethyl-3-(2-phosphono-2-methylphosphino-ethyl)-1-methylpyridinium Iodide 2-(3-pyridinyl)ethylidene phosphonomethyl phosphinic acid triethyl ester (2.32 g, 6.64 mmol) and iodomethane (9.42 g, 6.44 mmol) are heated at reflux for 24 hours in dry acetone (23 ml) under nitrogen. The reaction mixture is evaporated in vacuo to dryness, acetone is added and the mixture evaporated in vacuo to dryness a second time to provide the N-methylated adduct (2.60 g).

III. Synthesis of 3-(2-Phosphono-2-methylphosphinoethyl)-1-methylpyridinium Iodide The N-methyl pyridinium adduct (2.60 g, 6.20 mmol) is heated at reflux in 6N hydrochloric acid for 18 hours. The reaction mixture is evaporated in vacuo to dryness, methanol is added and the mixture evaporated to dryness a second time. The crude product is dissolved in a minimum volume of water and then filtered through silica gel. The aqueous filtrate is evaporated in vacuo to yield 0.5 g (25% yield for two steps) of the N-methyl pyridinium phosphonomethylphosphinic acid.

EXAMPLE 10

Synthesis of 3-(2-Phosphono-2-sulfonoethyl)-1-methylpyridinium Chloride $$\text{Cl}^- \quad \text{pyridinium ring with } -\text{CH(SO}_3\text{H)}-\text{P(O)(OH)}_2 \text{ substituent; N}^+-\text{CH}_3$$

The compound above is prepared and synthesized as described hereinbelow.

I. Synthesis of Triethyl-2-(3-pyridinyl)ethylidene-1-phosphono-1-sulfonate

To a mixture of NaH (1.10 mmol) 40% in oil and toluene (100 ml) is added diethoxyphosphinyl methanesulfonic acid, ethyl ester (1.00 mmol) [prepared as described by J. C. Carretero, et. al., Tetrahedron, Vol. 43, pp. 5125–5134 (No. 21) 1987] at 0° C. under an atmosphere of nitrogen. After stirring 30 minutes, the reaction mixture is added dropwise via an addition funnel to 3-picolyl chloride (1.00 mmol) in toluene (50 ml) at room temperature. Stirring is continued for 12 hours, the reaction mixture is poured into water and the layers are separated. The aqueous layer is extracted with diethyl ether twice and the combined organic layers are washed with saturated aqueous sodium chloride. The product is separated from unreacted starting materials by flash chromatography on silica gel with 10% isopropyl alcohol in methylene chloride. This provides the phosphonosulfonate in a yield as a pale yellow oil.

II. Synthesis of Triethyl-3-(2-phosphono-2-sulfonoethyl)-1-methylpyridinium Iodide A solution containing (triethyl-2-(3-pyridinyl)ethylidene-1-phosphono-1-sulfonate) (5.0 mmol), iodomethane (25.0 mmol) and dry acetonitrile (100 ml) is heated at reflux for 72 hours. The reaction mixture is evaporated in vacuo to dryness, acetone is added and the mixture evaporated to dryness a second time. The crude product is triturated in hexanes/diethyl ether, collected by filtration under nitrogen and dried in a vacuum desiccator to yield the N-methyl pyridinium adduct.

III. Synthesis of 3-(2-Phosphono-2-sulfoethyl)-1-methylpyridinium Chloride

The N-methylpyridinium salt (0.3 mmol) is hydrolyzed in refluxing 6N hydrochloric acid (10 ml) for 12 hours. The reaction mixture is evaporated in vacuo to dryness. The crude product is dissolved in a minimum amount of water and treated with charcoal then filtered through celite. The filtrate is poured into ethanol to precipitate the product and the precipitate is collected by filtration and dried in a vacuum desiccator to provide 3-(2-phosphono-2-sulfoethyl)-1-methylpyridinium Chloride.

EXAMPLE 11

Synthesis of 2-(2-hydroxy-2,2-diphosphonoethyl)-1,1-dimethyl piperidinium Iodide

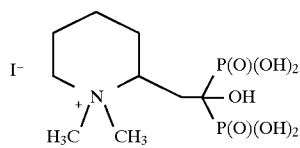

I. Synthesis of [1-hydroxy-2-(2-piperidinyl)ethylidene]-bis[phosphonic Acid] Monosodium Salt

[1-hydroxy-2-[(2-(pyridinyl)ethylidene]bis[phosphonic Acid], prepared as described in Example 5, Part I, hereinbefore, (2.5 g, 0.0088 mole) is added to 50 ml of water and the pH is adjusted to 6.0 with 50% NaOH. This solution is placed in a 500 ml Parr hydrogenation bottle and approximately 1 g of 10% Pd/C catalyst is added. The Parr bottle is placed on a Parr hydrogenator apparatus and pressed to 45 psi of H$_2$ gas. After 4 hours, more catalyst is added and the pressure is brought back to 45 psi and allowed to react overnight. The solution is filtered through celite, washed with water and evaporated down to a clear oil. Ethanol is added (30 ml) to the oil and the mixture is gently refluxed for 48 hours to convert the oil to a powdery, white precipitate. This is filtered and washed with ethanol.

II. Synthesis of 2-(2-Hydroxy-2,2-diphosphonoethyl)-1,1-dimethylpiperidinium Iodide Salt

[1-Hydroxy-2-(2-pyridinyl)ethylidene]bis[phosphonic acid] monosodium salts (3.5 mmol) is dissolved in a mixture of DMSO (10 ml) and water (50 ml). To this is added methyl iodide (35.0 mmol) and the solution is heated at reflux under an atmosphere of nitrogen for 3 days. The reaction mixture is concentrated under reduced pressure and the quaternized product purified by recrystallization from water and isopropanol.

EXAMPLE 12

Synthesis of 3-[2,2-Diphosphono-2-hydroxyethyl]-1,1-dimethyl piperidinium Iodide

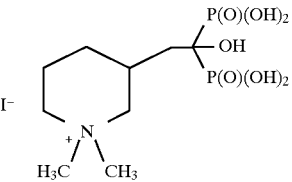

I. Synthesis of [1-Hydroxy-2-(3-piperidinyl)ethylidene]bis[phosphonic acid]Monosodium Salt

[1-Hydroxy-2-(3-pyridinyl)ethylidene]bis[phosphonic acid], prepared as described in Example 3, Part I, hereinbefore, (2.0 g, 0.0071 mole) is added to 50 ml of water and the pH is adjusted to 6.0 with 50% NaOH. This solution is placed in a 500 ml Parr hydrogenation bottle and approximately 1 g of 10% Pd/C catalyst is added. The Parr bottle is placed on a Parr hydrogenator apparatus and pressed to 45 psi of H2 gas. After 4 hours, more catalyst is added and the pressure is brought back up to 45 psi and allowed to react overnight. The solution is filtered through celite, washed with water and evaporated down to a clear oil. Ethanol is added (30 ml) to the oil and the mixture is gently refluxed for 1 hour to convert the oil to a powdery, white precipitate. This is filtered and washed with ethanol.

II. Synthesis of 3-[2,2-Diphosphono-2-hydroxyethyl]-1,1-dimethyl piperidinium Iodide Using essentially the same procedure as described in Example 11, Part II, hereinbefore, [1-hydroxy-2-(3-piperidinyl)ethylidene]bis[phosphonic acid] monosodium salt is converted to 3-[2,2-diphosphono-2-hydroxyethyl]-1,1-dimethylpiperidinium iodide.

EXAMPLE 13

Synthesis of 3-(2-Carboxy-2-phosphonethyl)-1-methylpyridinium Chloride

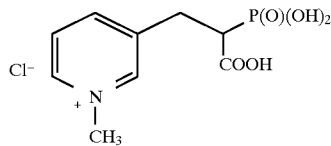

The above compound is prepared and synthesized as described herein below.

I. Synthesis of Trimethyl 2-Phosphono-3-(3-pyridyl) propanoate

Solution A is prepared by adding 2.00 g (0.050 mole) of NaH (60% in mineral oil) slowly to a solution of 8.09 ml (0.050 mole) of trimethyl phosphonoacetate in 50 ml of anhydrous DMSO to minimize foaming. The reaction mixture is a light yellow solution. (All of the above is done at ambient temperature in oven-dried glassware under a nitrogen atmosphere).

To a mixture of 8.20 g (0.050 mole) of 3-picolyl chloride hydrochloride in 50 ml of anhydrous dimethylsulfoxide under nitrogen is slowly added (over 5 minutes to minimize foaming) 2.0 g (0.050 mole) of NaH (60% in mineral oil).

The reaction is stirred for 75 minutes. To this reaction mixture is added Solution A over a 40 minute period. The resulting solution is stirred at ambient temperature for 18 hours. The solvent is removed under vacuum to yield a sticky reddish-brown material. Said material is taken up in 100 ml of saturated $NH_4Cl$ solution (aqueous), and is extracted with 3×100 ml of methylene chloride. The extracts are combined, dried with $MgSO_4$, and evaporated dry in vacuo to afford 11.3 g of oil. Mineral oil is extracted from this with 3×100 ml hexane, leaving 9.6 g of red-brown material. This is purified by preparative HPLC, using acetone as eluant on a silica gel column. 2.5 g of the desired product is recovered.

II. Synthesis of 3-(2-Carboxy-2-phosphonoethyl)-1-methyl-Pyridinium Chloride

A solution of 2.5 g (0.009 mole) of trimethyl 2-phosphono-3-(3-pyridyl)propanoate and 2.25 ml (0.020 mole) of methyl iodide in 5 ml of dry tetrahydrofuran is stirred at ambient temperature for 18 hours. A gum forms during this time. The solvent is poured off, and the gum is washed with 2×10 ml of dry ether.

The ester groups are hydrolyzed by dissolving the gum in 25 ml of 6N HCl, and refluxing the resulting solution for 3 hours. The solution is cooled, and is extracted with 3×8 ml of $CHCl_3$, which removed some I2. The aqueous layer is evaporated under vacuum to give a brownish gum. This is dissolved in 20–25 ml of hot, absolute ethanol. The solution is cooled, and 10–15 ml of dry acetone was added. Upon stirring for 14 hours at ambient temperature a solid forms. This is filtered off and washed with acetone and then with ether, yielding 2.0 g of pale yellowish solid. This is further purified by stirring it with 10 ml of anhydrous ethanol for 2.5 hours, then filtering and washing with 3 ml ethanol, then with 10 ml acetone, then with ether. There is obtained 1.82 g (71% yield) of 3-(2-carboxy-2-phosphonoethyl)-1-methylpyridinium chloride.

EXAMPLE 14

Synthesis of 3-(3,3-diphosphonopropyl)-1-hexadecylpyridinium, disodium salt

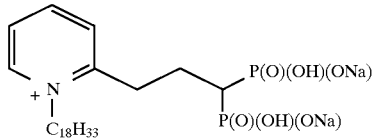

I. Synthesis of [3-2-pyridinyl)propylidene]bis[phosphonic acid]tetraethyl ester

Phenyllithium (79 ml, 1.96M in ether, 0.155 mol) in 200 ml of dry benzene is cooled to 0° C. and 2-picoline (12.3 g, 0.132 mol) is added dropwise in 50 ml of benzene. The reaction is stirred for 3 hours and tetraethyl ethenylidenebis (phosphonate) is added dropwise in 50 ml of benzene. The reaction is allowed to warm to room temperature and is stirred overnight. 1N HCl (132 ml) is added with cooling and the layers are separated. The pH of the aqueous phase is adjusted to 10 and several extractions with ethyl acetate are done. The combined extracts are dried over sodium sulfate, then filtered and evaporated to give 47.2 g of [3-2-pyridinyl) propylidene]bis[phosphonic acid] tetraethyl ester. This crude product is purified in portions before use by flash chromatography with 7% $MeOH/CHCl_3$. For example, 13.2 g of product is chromatographed in two portions to give 8.2 g of purified product.

II. Synthesis of 3-(3,3-diphosphonopropyl)-1-hexadecylpyridinium iodide, tetraethyl ester The tetraethyl bis(phosphonate), prepared as described in part I, hereinabove (8.2 g, 20.9 mmol) is taken up in 50 ml of acetonitrile. Iodohexadecane (22 g, 62.5 mmol) is added and the mixture is refluxed for three days. The solvent is evaporated and the residue is placed on a dry 10 inch bed of silica gel which is then eluted with 5% $MeOH/CHCl_3$. The excess iodohexadecane elutes in the first three fractions. Product is collected in several fractions. The first three fractions are combined to give 5.3 g of product and the next 8 fractions are combined to give 7.8 g of product providing a total of 13.1 g.

III. Synthesis of 3-(3,3-diphosphonopropyl)-1-hexadecylpyridinium, disodium salt The tetra ester (7.8 g, 10.5 mmol) is refluxed in 75 ml of 6N HCl for 2 days. The reaction is cooled and extracted with ethyl acetate. The aqueous phase is evaporated, methanol is added and the solution is again evaporated to yield 5.4 g of product. 1N sodium hydroxide (17 ml is added and the pH adjusted to 7. The solution is freeze-dried to give 5.6 g of 3-(3,3-diphosphonopropyl)-1-hexadecylpyridinium disodium salt (79%) as approximately the disodium salt.

EXAMPLE 15

Synthesis of (7-diphosphonohydroxymethyl)-2-methyl-2-pyrindinium iodide

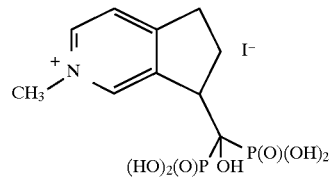

I. Synthesis of N-(2,2-diethoxyethyl)-N-[(3-methoxyphenyl) methyl]-4-methylbnezenesulfonamide m-Anisaldehyde (112 g, 0.82 mol) and aminoacetaldehyde diethyl acetal (115 g, 0.86 mmol) in benzene (2.6 l) are heated at reflux under an atmosphere of nitrogen for 3 hours. Approximately 1.8 l of benzene is then removed by concentration under reduced pressure. The remaining solution is placed in a Parr hydrogenation vessel and hydrogenated at room temperature until the theoretical amount of hydrogen (56 lb.) is taken up. The solution is then filtered through celite and the filtrate is concentrated under reduced pressure. The resulting oil is dissolved in pyridine (1 l) and to this is added dropwise p-methoxybenzene sulfonyl chloride (172 g, 0.90 mol) in pyridine (600 ml). The reaction mixture is allowed to stir for 3 days at room temperature and then concentrated under reduced pressure. The residue is poured into ice water and stirred at 0° C. for 1 hour. The aqueous mixture is extracted with diethyl ether (6×500 ml). The combined organic extracts are washed with saturated aqueous NaCl, dried over magnesium sulfate, filtered and concentrated under reduced pressure to provide the product (312 g) in a 93% yield as a yellow oil.

II. Synthesis of 7-Methoxyisoquinoline

To a 2 liter round bottom flask equipped with a magnetic stir bar, condenser and nitrogen inlet is added (75 g, 0.184 mole) of N-(2,2-diethoxyethyl)-N-[(3-methoxyphenyl) methyl]-4-methyl-benzenesulfonamide, 1.0 liter of dioxane and 200 ml of 6N HCl. This slurry is stirred and heated at reflux under nitrogen for 18 hours. The reaction solution is then slowly poured into 1 liter of $H_2O$ and stirred for an additional 30 minutes then extracted with ether (2×500 ml).

The pH of the aqueous layer is adjusted to 8 with ammonium hydroxide, the product is extracted with dichloromethane. The combined organics extracts are dried over MgSO$_4$, filtered and evaporated to yield 30 g of an oil. The crude product is purified by chromatography with 12.0% acetone in dichloromethane to provide the product (19.7 g) in a 67% yield.

III. Synthesis of 7-Hydroxyisoquinoline

To a 2-liter, 3-necked round bottom flask equipped with a magnetic stir bar and addition funnel is added 19.7 g (0.124 mole) 7-methoxyisoquinoline and 800 ml of dry dichloromethane. This solution is stirred and cooled to −75° C. with a dry ice/acetone bath, 628 ml (0.628 mole) of 1.0M boron tribromide in dichloromethane is added dropwise maintaining the temperature at −75° C. Thereafter the slurry is stirred for 18 hours allowing the temperature to rise to room temperature. The reaction slurry is poured into 1 liter of ice water and stirred for an hour. The layers are separated and the aqueous layer is then adjusted from acidic to neutral (pH 7) with 1N NaOH. A yellow solid precipitates and is filtered off, then air dried to yield 14.5 g of a yellow solid, 81%.

IV. Synthesis of 7-Hydroxy-8-nitroisoquinoline

To a 300 ml round bottom flask is added 14.5 g (0.1 mole) of 7-hydroxyisoquinoline and 100 ml of warmed tetramethylene sulfone. The brown slurry is stirred and to it is added portionwise 18.6 g (0.14 mole) of nitronium tetrafluoroborate with cooling (ice bath). The reaction is stirred for 3 hours. The reaction is then quenched with 100 ml of methanol, evaporated to dryness and triturated twice with ether to precipitate a dark solid (19.0 g, 100%).

V. Synthesis of 8-Amino-7-hydroxylisoquinoline HCl salt

A hydrogenation jar is charged with 7-hydroxy-8-nitroisoquinoline (28.5 g, 0.15 mol), 5% Pd on carbon (6.0 g) and ethanol (725 ml). The slurry is hydrogenated (40 psi) until hydrogen uptake stops. The reaction mixture is then filtered through celite and the filtrate is concentrated under reduced pressure. The residue is dissolved in methanol. Addition of etheric-HCl precipitates the product as an HCl salt (19 g) in 65% yield.

VI. Synthesis of 7-hydroxy-8-isoquinolinediazonium chloride To 8-amino-7-hydroxyisoquinoline HCl salt (4.94 g, 0.025 mol) in ethanolic-HCl at 0° C. is added dropwise a solution of tert-butylnitrite (17.46 ml), ethanol (790 ml) and water (58 ml). Following completion of the addition, the solution is stirred an additional 2 hours at 0° C. The product is precipitated from the reaction mixture by the addition of diethyl ether (2 l). The product is collected by filtration and rinsed with diethyl ether to provide the desired product (2.6 g) in 50% yield.

VII. Synthesis of 2-pyrindine-7-carboxylic acid, methyl ester

7-Hydroxy-8-isoquinolinediazonium chloride (0.50 g, 2.4 mmol) and sodium bicarbonate (302 mg, 3.6 mmol) in anhydrous methanol (650 ml) is irradiated with a 275 watt sunlamp at 0° C. for 3 hours. The reaction mixture is evaporated to dryness under vacuum. The crude residue is dissolved in water and the product is extracted in methylene chloride. The combined organic extracts are dried over magnesium sulfate, filtered and concentrated under reduced pressure to provide the product as an orange solid (210 mg) in 50% yield.

VIII. Synthesis of Dihydro-2-pyrindine-7-carboxylic acid, methyl ester

A hydrogenation bottle is charged with 2-pyrindine-7-carboxylic acid, methyl ester (0.8 g, 4.57 mmol), 5% Pd on carbon (2.0 g, wet) and methanol (125 ml). The slurry is hydrogenated (40 psi) until hydrogen uptake stops. The reaction mixture is filtered through celite and then evaporated to dryness to provide the product (430 mg) in 53% yield.

IX. Synthesis of Dihydro-2-pyrindine-7-carboxylic acid, HCl salt

Dihydro-2-pyrindine-7-carboxylic acid, methyl ester (0.53 g, 3.0 mmol) is heated at 58° C. in 1N NaOH (3.1 ml) and methanol (30 ml) for 2.5 hours. The solution is evaporated to dryness under vacuum and the resulting residue is stirred in ethanolic-HCl to precipitate the product. The desired product is collected by filtration.

X. Synthesis of [1-hydroxy-(dihydro-2-pyrind-7-yl)methylene]-bis[phosphonic acid]

To phosphorus trichloride (1.19 g, 8.63 mmol) is added a slurry of dihydro-2-pyrindine-7-carboxylic acid, HCl salt (0.54 g, 2.88 mmol), phosphorous acid (708 mg, 8.63 mmol) and chlorobenzene (10 ml). The reaction mixture is stirred and heated at 105° C. for 4 hours. The mixture is then cooled to room temperature and the chlorobenzene is decanted off. To the crude residue is added 1N HCl (10 ml) and the mixture is heated at reflux overnight. The reaction mixture is then concentrated under reduced pressure and triturated in acetone to provide the desired product (107 mg) in good purity.

XI. Synthesis of (7-diphosphonohydroxymethyl)-2-methyl-2-pyrindinium iodide

Using essentially the same procedure as described in Example 3, part II, hereinbefore, [1-hydroxy-(dihydro-2-pyrind-7-yl)methylene]bis[phosphonic acid] is converted to (7-diphosphonohydroxymethyl)-2-methyl-2-pyrindinium iodide.

EXAMPLE 16

Synthesis of 3-(2,2-Diphosphonoethyl)-N,N,N-trimethyl-benzenaminium hydroxide, Inner salt

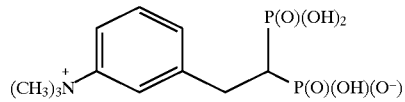

3-(2,2-Diphosphonoethyl)-phenyl-trimethyl ammonium salt is prepared and synthesized as described herein below.

I. Synthesis of 2-[3-nitrophenylethylidene]bis[phosphonic acid]tetraethyl ester

To a flame-dried 50 ml round bottom flask under a nitrogen atmosphere is added 1.12 g of potassium hydride (35% in oil, 10.59 mmol) which is first washed with pentane. Dry toluene (10 ml) is added and the suspension is cooled to 0° C. Tetraethyl methylene diphosphonate (3.31 g, 9.63 mmol) is added dropwise and when the addition is complete, the mixture is allowed to stir at room temperature for 1 hour. 3-Nitrobenzyl bromide (2.09 g, 9.63 mmol) is dissolved in 10 ml of toluene in a 100 ml flask and the anion solution is added to it and allowed to stir overnight at room temperature. The reaction mixture is filtered through celite and then concentrated under reduced atmosphere. The crude residue is purified by preparatory liquid chromatography to provide 2-[3-nitrophenylethylidene]bis[phosphonic acid] tetraethyl ester.

II. Synthesis of 2-[3-aminophenylethylidene]bis[phosphonic acid]

2-[3-Nitrophenylethylidene]bis[phosphonic acid] tetraethyl ester is dissolved in ethanol (50 ml) and to this is added 10% palladium on carbon (0.50 g). The reaction mixture is shaken under pressure (40 psi) in a Parr hydrogenation bottle for 2 hours until hydrogen uptake was complete. The reaction mixture is filtered through celite. The celite is washed with fresh ethanol and then the filtrate and ethanol washings are combined and concentrated under reduced pressure. The residue is dissolved in chloroform and then the amino adduct is isolated as the HCl salt by extraction into 6N HCl. The aqueous layer containing the amino product as a tetraethyl ester is heated at reflux for 12 hours under an atmosphere of nitrogen. The reaction mixture is cooled, treated with charcoal and then filtered through celite. The filtrate is concentrated under reduced pressure to provide the bisphosphonic acid.

III. Synthesis of 3-(2,2-Diphosphonoethyl)-phenyltrimethyl ammonium salt

2-[3-Aminophenylethylidene]bis[phosphonic acid] is dissolved in water (10 ml) and ethanol (2 ml). To this is added iodomethane in excess and the reaction mixture is heated at reflux under an atmosphere of nitrogen for 48 hours. The reaction mixture is cooled and concentrated under reduced pressure and the crude residue is recrystallized from water and ethanol to provide the benzenaminium salt as a white solid.

EXAMPLE 17

Schenk Model

The compounds are evaluated for in vivo bone resorption inhibition and mineralization inhibition in an animal model system known in the field of bone metabolism as the Schenk Model. The general principles of this model system are disclosed in Shinoda et al., *Calcif. Tissue Int.*, 35, 87–99 (1983); and in Schenk et al., *Calcif. Tissue Res.* 11, 196–214 (1973), the disclosures of which are incorporated herein by reference.

Materials and Methods:

Animals

Preweaning 17-day-old (30 gms) male Sprague Dawley rats (Charles River Breeding Laboratories) are shipped with their mothers and placed in plastic cages with their mothers upon arrival. At 19 days of age, pups receiving Rat Chow and water ad libitum are randomly allocated into treatment or control groups comprising seven animals per group. On day 1 and again on day 7 all animals are given an intraperitoneal ("IP") injection of Calcein (1% solution in 0.9% saline solution; dosed at 0.2 ml/100 g body weight). On day 4 all animals are given an IP injection of tetracycline hydrochloride (1% solution in 0.9% saline solution; dosed at 0.2 ml/100 g body weight). These compounds label actively mineralizing bone and cartilage.

Dose Solutions and Dosing Procedure

All solutions are prepared for subcutaneous injection in 0.9% normal saline and adjusted to pH 7.4 using NaOH and/or HCl. Dose solution calculation is made by considering the mass of powder (based on molecular weight, hydration) of the active material in mg/kg (body weight) that corresponds to mgP/kg. Concentrations are based on dosing 0.2 ml/100 g body weight. Typically, all compounds are administered at 0.01, 0.1, 1.0 and 10.0 mg P/kg/day for 7 days. Compounds showing activity at 0.1 mg P/kg/day are then tested at logarithmic decrements down to 0.001 mg P/kg/day. Adjustments in dosage based on changes in body weight are made on a daily basis.

Necropsy, Tissue Processing and Histomorphometry

On day 8 after the start of dosing, all animals are sacrificed by IP overdose of pentabarbitol. Tibias are dissected free and placed in 70% ethyl alcohol. One tibia is dehydrated in graded ethanol solutions and embedded in methyl methacrylate as described in Schenk, *Methods of Calcified Tissue Preparation* (G. R. Dickson, Editor; Elsevier Science Publ., The Netherlands; 1984), the disclosures of which are incorporated herein by reference in their entirety. The tibia is sectioned longitudinally through the metaphyseal area. Specimens are stained on one surface with silver nitrate and mounted on microscope slides for evaluation with a Quantimet Image Analyzer (Cambridge Instruments, Inc.) using both incandescent and ultraviolet illumination. Metaphyseal trabecular bone content is measured in the region between the fluorescent label and the growth plate: expressed as percent of total area (bone+marrow). Epiphyseal growth plate width is obtained as the mean value of 10 equally-spaced measurements across the section.

Statistical evaluation of data is made using parametric and non-parametric analysis of variance and Wilcoxons rank sum test to determine a statistically significant effect compared to control animals. The Schenk model provides data for in vivo bone resorption inhibition by the compounds.

EXAMPLE 18

Adjuvant Arthritis Model

There are numerous animal models of arthritis, among these is adjuvant-induced arthritis using *Mycobacterium butyricum*. This model in a number of ways mimics rheumatoid arthritis in the human (joint swelling associated with cellular and pannus invasion of the joint space, bone resorption, and release of chemotaxic factors and lysosomal constituents into the joint space) (1,2). A number of prophylactic and therapeutic studies have indicated the potential use of anti-inflammatory drugs (3,4) and diphosphonates in arthritis (5,6).

REFERENCES

1. Pearson, C., Wood F. (1959), Studies of Polyarthritis and Other Lesions Induced by Injection of Mycobacterial Adjuvant. 1. General Clinical and Pathological Characteristics and Some Modifying Factors, *Arth. Rheum.*, 2:440–459.
2. Blackman, A., Burns, J. W., Framer, J. B., Radziwonik, H., Westwick, J. (1977), An X-ray Analysis of Adjuvant Arthritis in the Rat. The Effect of Prednisolone and Indomethacin, *Agents and Actions*, 7:145–151.
3. Winter, C. A., Nuss, G. W. (1966), Treatment of Adjuvant Arthritis in Rats with Anti-inflammatory Drugs, *Arth. Rheum.*, 9:394–404.
4. Winder, C. V., Lembke, L. A., Stephens, M. D. (1969), Comparative Bioassay of Drugs in Adjuvant-Induced Arthritis in Rats: Flufenamic Acid, Mefenamic Acid, and Phenylbutazone, *Arth. Rheum.*, 12:472–482.
5. Francis, M. D., Flora, L. King, W. R. (1972), The Effects of Disodium Ethane-1-Hydroxy-1-Diphosphonate on Adjuvant Induced Arthritis in Rats, *Calcif. Tiss. Res.*, 9:109–121.
6. Flora, L. (1979), Comparative Antiinflammatory and Bone Protective Effects of Two Diphosphonates in Adjuvant Arthritis, *Arth. Rheum.*, 22:340–346.

Adjuvant arthritis is a severe cellulitis and synovitis induced in male rats (either Sprague Dawley or Lewis strain) by a single subcutaneous (SC) injection of *Mycobacterium butyricum* (8 mg/ml) in mineral oil on day 0. The compounds are dosed once daily either orally (PO) or parenterally (SC) and can be tested in either prophylactic (from day 0) or therapeutic (from day 9 or 10 or 14) protocols. Antiarthritic efficacy can be measured as a reduction in paw volume, body weight loss, bone loss or reactive new bone formation compared to the saline-treated arthritic controls. Treatment can be stopped and the "flare" response (rapid increase in inflammation) examined, which indicates a compound's ability to maintain efficacy.

Materials and Methods

A. Animals

Animals used are male Lewis rats (LEW). On arrival, the rats are randomized by computer generated random numbers and placed in individual wire suspended cages. Food and water are administered ad libitum, throughout the entire study. Routine care and maintenance of the animals are performed according to State and Federal regulations. Each rat is identified with a number placed in front of the cage and on the tail of the rat.

B. Experimental Design

On day 1 body weights (BW) and hind paw volume [(PV) recorded by a mercury displacement method using a pressure transducer linked into a computer] measurements are taken on all rats. On day 0, the induction of arthritis using MFA [*Mycobacterium butyricum* (Mb) 4.4 mg/kg in oil] is as follows: rats are anesthetized and receive a single SC injection of MFA at the base of the tail under aseptic conditions.

Paw volumes and body weights are measured thereafter on various days, usually twice a week. For the prophylactic protocol, rats are randomly allocated into groups of 8–10 rats and treatment begins on day 0 and continues daily until termination. For the therapeutic protocol, the rats are randomized into treatment groups of 8–10 rats according to their PV on day 10. Dosing begins on day 10 and continues daily until termination. For both protocols, animals are placed in shoe box cages with deep bedding on or before day 10.

Dosing Solutions

For Drugs Unlikely to Oxidize

Drugs are weighed out on a calibrated balance and then mixed with distilled water in a volumetric flask. The solution is adjusted to pH 7.4 with 01N NaOH. Then the solution is filtered through a 0.45 μm sterile filter into a sterile storage container. When not in use, the solution is stored in the refrigerator.

For Drugs Likely to Oxidize

Drugs are weighed out on a calibrated balance and then mixed with deoxygenated water in a volumetric flask. The stock solution is filtered through a 0.45 μm sterile filter into a sterile storage container. When not in use, the stock solution is kept refrigerated.

On a daily basis, a specific amount of solution is removed from the stock solution, put into small dosing beaker and then adjusted to pH 7.4 according to a predetermined calculation. Further dilutions of the adjusted solution can be made if necessary (with deoxygenated water).

Drug calculations are made based on the molecular weight, the purity of the compound, the amount based on mg/kg (body weight) and the desired final concentration in mgP/kg. The volume dosed per rat is 0.1 ml/100 gm of body weight subcutaneously, given as an injection in the inguinal fold of the animal, alternating sides each day or 1 ml/200 gm BW given orally using a curved stainless steel dosing tube. Adjustments based on changes in body weight are made weekly.

Radiographs, Necropsy and Tissue Collection

At termination, each rat is sacrificed with 1 ml Socombe® intraperitoneally (IP). Immediately a whole body radiograph is taken by a Torrox 120D x-ray unit at MA=5, ISUP=50 and time=60 sec. on Kodak non-screen medical film. Hind legs are removed from each rat and fixed in 10% buffered formalin along with a piece of liver, kidney, spleen, and thimus. The tibiotarsal joints are decalcified in 4% EDTA, pH 7.4 and processed routinely in paraffin blocks and H+E stain. The organ parts also processed in paraffin and stained H+E.

The histology sections are evaluated qualitatively for bone and soft tissue lesions using light microscopy. Radiographs are graded for bone resorption (BR) in 6 anatomical trabecular bone sites in each hind leg and 4 sites in each front leg on a scale of 0–3 giving an arbitrary score of 0–60 for all 4 legs. For reactive new bone formation (RNB), radiographs are graded on a severity scale of 0–3 for the lateral and medical surfaces of the tibia and then 0–2 for all other areas mentioned above, giving an arbitrary score of 0–44.

D. Statistical Analysis:

Data analysis on paw volume, bone resorption and reactive new bone formation is performed by student's t-test and one-way analysis of variance with Tukeys (SAS) (12). Differences are considered significant at p=0.05 or less.

This model provides in vivo data for the efficacy of antiarthritic compounds in terms of reducing paw swelling bone loss and reactive new bone formation compared to the saline treated arthritic animals.

EXAMPLE 19

Capsules are prepared having the following composition:

|  | Mg Per Capsule |
|---|---|
| Active Ingredient | |
| 3-(2,2-diphosphonoethyl)-1-(2-mercaptoethyl) pyridinium chloride | 350.0 |
| Excipients | |
| Lactose | 90.0 |
| Microcrystalline Cellulose | 60.0 |
| Magnesium Stearate | 1.0 |

The capsules having the above composition are prepared using conventional methods as described below:

The active ingredient is mixed with the microcrystalline cellulose in a turn shell blender for approximately ten (10) minutes.

The resulting mixture is passed through a hammer mill with an 80 mesh screen.

The mixture is put back into the twin shell blender along with the lactose and is then mixed for approximately fifteen (15) minutes.

The magnesium stearate is next added and blended for an additional five (5) minutes. The resulting blend is then compressed on a piston-activated capsule filler.

Any of the compounds prepared according to Examples 1 to 13 and Example 15 may be substituted for the active ingredient in the capsule prepared hereinabove.

EXAMPLE 20

Tablets are prepared having the following composition:

|  | Mg Per Tablet |
|---|---|
| Active Ingredient | |
| 3-(2-hydroxy-2,2-diphosphonoethyl)-1-methyl pyridinium iodide disodium salt | 700.00 |
| Excipients | |
| Lactose (spray-dried) | 200.0 |
| Starch (1500) | 100.0 |
| Magnesium Stearate | 25.0 |

Tablets are prepared having the above composition using conventional methods as described below:

The active ingredient is ground in a ball mill for approximately thirty (30) minutes. The milled active ingredient is then blended in a twinblade mixer with the spray-dried lactose for approximately twenty (20) minutes.

The starch is added to the mixture and is then mixed for an additional fifteen (15) minutes. The blend is compressed into tablets on a standard tablet press.

Any of the compounds prepared according to Examples 1 to 13 and Example 15 may be substituted for the active ingredient in the tablet prepared hereinabove.

EXAMPLE 21

Injectable solutions are prepared by conventional methods using 10.0 ml of physiological saline solution and 7.0 mg P of 3-(2-hydroxy-2,2-diphosphonoethyl)-1-methylpyridinium hydroxy inner salt, adjusted to pH=7.4.

One injection, one time daily for 4 days, results in appreciable alleviation of hypercalcemia of malignancy in patients weighing approximately 70 kilograms.

Any of the compounds prepared according to Examples 1–16 may be substituted for the active ingredient in the injection prepared hereinabove.

EXAMPLE 22

The following is a representative toothpaste composition of the subject invention.

| Component | Wt % |
|---|---|
| 3-(3,3-diphosphonopropyl)-1-hexadecylpyridinium, disodium salt | 2.0 |
| Sorbitol | 33.0 |
| Saccharin | 0.46 |
| Silica | 22 |
| NaF | 0.243 |
| Glycerin | 9 |
| NaOH (50% Soln.) | 0.2 |
| Carbopol | 0.2 |
| Keltrol | 0.6 |
| $TiO_2$ | 0.5 |
| Sodium alkyl sulphate (28% Soln.) | 4 |
| PEG 6 | 3 |
| FD&C Blue #1 (1% Soln.) | 0.05 |
| Flavor | 1.1 |
| Water | q.s. |

First, mechanically mix the $TiO_2$, silica, carbopol and X-gum (Keltrol). These are all solids. Set aside. Second, dissolve the active (2% of the pyridinium diphosphonate) in water and adjust to approximately pH=7. Then dissolve the NaF, sorbitol, saccharin, glycerin, PEG 6 and F&DC Blue #1 (1% soln) into the aqueous mixture. Then add the sodium alkyl sulfate (28% soln.), NaOH and finally flavor to the aqueous mixture. Then add the solid mix, making sure that thorough and sufficient mixing of the paste occurs (temperature should not exceed 150 ° F.) and that the carbopol and X-gum are dissolved. Check final pH at this stage and adjust to pH=7.0 if necessary. (Do this by spinning down a 1:4 slurry of said dentifrice in water and testing pH of the supernatant.)

EXAMPLE 23

The following is a representative example of a mouth rinse composition of the subject invention.

| Component | Wt % |
|---|---|
| 3-(3,3-diphosphonopropyl)-1-hexadecylpyridinium, disodium salt | 0.1 |
| EtOH (200 proof) | 16.25 |
| Surfactant (TWEEN 80) | 0.12 |
| Glycerin | 10 |
| Saccharin | 0.06 |
| Flavor | 0.041 |
| F&DC Blue #1 (1% soln) | 0.022 |
| F&DC Yellow #5 (1% soln) | 0.018 |
| Benzoic acid | 0.0045 |
| Sodium Benzoate | 0.054 |
| Water | q.s. |

First, dissolve active (say 0.5%) in the water and adjust to pH=7 with NaOH if necessary. Then add EtOH, glycerine, saccharin, F&DC Blue #1, F&DC Yellow #5, benzoic acid and NaBenzoate. Dissolve the flavoring in the surfactant and add this mixture to the above ingredients. Check pH and adjust if necessary.

EXAMPLE 24

A Caucasian male, weighing approximately 92 kilograms, seventy-two years of age, suffering from moderate to severe pain, and occasional swelling, of the right knee. After approximately one year of steadily increasing discomfort, he visits a physician who renders a clinical diagnosis of osteoarthritis of the right knee, which was subsequently verified by X-ray diagnosis.

After a period of ameliorative therapy of various NSAIDs, including aspirin, naprosen, and ketoprofen, his symptoms continue to worsen and his condition appears to degenerate. He returns to his physician who then prescribes the tablets prepared as described in Example 20 twice daily two hours before or after meals for a period of three months. His clinical symptoms of pain and swelling, particularly with extended walking, improved significantly after his 3 months of therapy. At the conclusion of three months at a dosage of 2 tablets per day, the therapy is continued at one-half the dosage originally prescribed (i.e. 1 tablet per day) indefinitely.

EXAMPLE 25

A black female, weighing approximately 65 kilograms, fifty-five years of age, presents with swelling and deformation of the finger joints of both hands, with partial loss of strength and/or dexterity of her fingers and hands. Upon visual and X-ray examination and various appropriate clinical tests approved by the American Rheumatological Association (ARA) she is diagnosed with rheumatoid arthritis.

After an unsuccessful analgesic and anti-inflammatory therapy, her physician prescribes the tablets prepared in Example 20, two times daily two hours before or after meals for a period of four months. After a month of therapy, her symptoms of knuckle swelling noticeably improves and her range of finger motion increases significantly; she continues therapy for the remainder of the four months, after which her physician continues the prescribed dose for an additional two months.

EXAMPLE 26

A female of Hispanic origin, twelve years of age, weighing approximately 37 kilograms, presents to the physician with idiopathic juvenile rheumatoid arthritis. Her symptoms include marked inflammation of multiple joints, complicated by heat and tenderness and indicating rapid and pathological degeneration of joint function.

Her physician refers her to a rheumatologist who immediately prescribes aggressive therapy by IV administration of the solution prepared as described in Example 21 over a period of three days, at the rate of 1 injection per day, administered over two hours. At the conclusion of the IV regimen, the physician prescribes the tablets prepared as described in Example 20, for a period of two months, during which she exhibits marked improvement with increased mobility and decreased pain. For the succeeding two months, the physician reduces her dose to ¾ of the original oral dose by prescribing 3 tablets over a period of two days, i.e. one 2-tablet day alternating with one 1-tablet day. At the conclusion of this regimen the dosage is again reduced to ¼ of the original dose by giving her the capsules prepared as described in Example 19, 1 capsule every day for an additional four months.

EXAMPLE 27

A 17-year-old Caucasian male visits a dentist for the first time in five years for a routine check-up. Visual examination of the patient's oral cavity reveals plaque and calculus buildup on the lingual surfaces of the lower incisors and on the distal surface of the upper molars. A routine mechanical cleaning is performed in an unsuccessful attempt to remove the plaque and calculus buildup. The dentist has the patient rinse his oral cavity with 15 ml of a 0.1% by weight oral solution of 3-(3,3-diphosphonopropyl)-1-hexadecylpyridinium, disodium salt prepared as described in Example 23 for one minute. The plaque and calculus are easily and painlessly removed by mechanical means. The dentist then prescribes a prophylactic regimen consisting of brushing with a dentifrice containing 3-(3,3-diphosphonopropyl)-1-hexadecylpyridinium, disodium salt prepared as described in Example 22. Said prophylactic regimen consists of brushing once daily for three minutes with said dentifrice for a period of three months. At the end of three months the patient's plaque and calculus problem is under control. The patent is permitted to use regular toothpaste and his dentist prescribes an anti-calculus, anti-plaque maintenance regimen consisting of rinsing the oral cavity once daily with a 0.1% solution of 3-(3,3-diphosphonopropyl)-1-hexadecylpyridinium, disodium salt.

EXAMPLE 28

A 60-year-old black female suffering from a painful gingivitis visits a dentist for the first time in ten years. Visual examination of her oral cavity reveals severe plaque and calculus buildup along the gumline. An attempt at mechanical removal of the plaque and calculus proves to be very painful for the patient. The dentist has the patient rinse her oral cavity three times, for one minute each time, with 10 mls of a 0.1% by weight solution of 3-(3,3-diphosphonopropyl)-1-hexadecylpyridinium, disodium salt. The plaque and calculus are easily removed by gentle mechanical means. The dentist then prescribes a treatment regimen consisting of brushing twice, for one minute at a time daily with a dentifrice containing 2.0% by weight of 3-(3,3-diphosphonopropyl)-1-hexadecylpyridinium, disodium salt. Said regimen continues for six months. The patient revisits the dentist, her plaque and calculus problem is under control and her gingivitis is improved. The dentist prescribes a maintenance regimen of a once daily oral rinsing with 10 mls of a 0.1% by weight solution of 3-(3,3-diphosphonopropyl)-1-hexadecylpyridinium, disodium salt. Said regimen continues for six months. The patient revisits the dentist; her plaque and calculus problem is under control and her gingivitis is improved. The dentist prescribes a maintenance regimen of a once daily oral rinsing with 10 mls of a 0.1% solution of 3-(3,3-diphosphonopropyl)-1-hexadecylpyridinium, disodium salt and a once daily brushing with a toothpaste containing 2% by weight of 3-(3,3-diphosphonopropyl)-1-hexadecylpyridinium, disodium salt.

EXAMPLE 29

A 60-year-old Caucasian female weighing 62 kg, experiences severe back pain. Her physician, with the aid of a radiologist, diagnoses her as having a crush fracture of the L1 vertebrae presumably due to osteoporotic bone loss. The patient is prescribed a three month, once-daily dosage regimen of a 700 mg tablet prepared according to the procedure described in Example 20. The 700 mg capsule is taken either two hours before or two hours after any given meal. After three months, the dosage is reduced to a 350 mg capsule, prepared as described in Example 19, taken every other day for a period of three months. Her physician then puts her on a maintenance dosing regimen wherein she takes a 100 mg capsule, prepared according to the procedure described in Example 19, every day for six months. After six months on the maintenance dosing regimen the patient is not experiencing any further back pain. Follow-up x-rays reveal no additional fractures.

EXAMPLE 30

A 75-year-old Oriental female weighing 53 kg suffers a fractured hip after a fall. She is hospitalized and diagnosed as having osteoporosis. A treatment regimen of calcitonin injections is prescribed. The calcitonin injections are painful to the patient and she is unable to comply with said calcitonin treatment. Her physician then switches her therapy to an oral phosphonate regimen. She is administered a 700 mg tablet prepared as described in Example 20, twice daily for one month. At the end of this one month of therapy, she is given a 700 mg tablet, once daily for two months. At the end of this two month period, she is given a 100 mg capsule, prepared according to the procedure described in Example 19, daily for three months. A follow-up visit to her physician reveals no apparent decrease in mineral density of the forearm as determined by photonabsorptimetry.

EXAMPLE 31

A 85-year-old Native American male weighing 65 kg presents to his physician with severe back pain. X-rays reveal multiple minor vertebral body collapse resulting from significant bone loss due to osteoporosis. The patient is prescribed a two month regimen of a 700 mg tablet and a 350 mg capsule to be taken on the same day, eight hours apart, prepared according to the procedures described in Examples 20 and 19 respectively. After two months on this regimen, his dosage is reduced to a 350 mg capsule once a day for two months. X-rays are then taken and an additional crush fracture is noted. He is then put on a maintenance regimen of a 100 mg capsule, once a day for six months. At the end of this six months, no significant apparent decrease in bone density is observed.

What is claimed is:

1. A quaternary nitrogen-containing phosphonate or the pharmaceutically-acceptable salts and esters thereof, having the following structure:

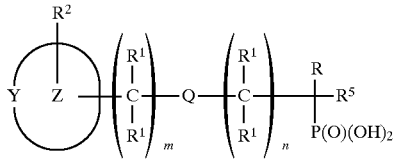

wherein m and n are integers from 0 to 10; m+n is from 0 to 10;

(a) Q is a covalent bond or a moiety selected from O, S, $NR^1$;

(b) Y is $N^+(R^8)_2$;

(c) Z is a five-membered saturated, unsaturated, or aromatic, monocyclic ring, wherein Z may contain an additional heteroatom selected from O, S, or N;

(d) R is $PO_3H_2$ or $P(O)(OH)R_4$, wherein $R_4$ is substituted or unsubstituted alkyl or 1–8 carbon atoms;

(e) Each $R_1$ is selected from the group consisting of nil; —$SR^6$; $R^9SR^6$; hydrogen; hydroxy; substituted or unstibstituted $C_1$–$C_8$ alkyl; —$OR^3$; —$CO_2R^3$; —$O_2CR^3$; —$NR^3{}_2$; —$N(R^3)C(O)R^3$; —$C(O)N(R^3)_2$; halogen; —$C(O)R^3$; arylalkyl; nitro; substituted or unsubstituted aryl, and combinations thereof;

(f) each $R_2$ is one or more substituents on the Z moiety independently selected from the group consisting of $N^+(R^8)_3$; —$SR^6$; $R^9SR^6$; hydrogen; substituted or unsubstituted $C_1$–$C_8$ alkyl; —$OR^3$; —$CO_2R^3$; —$O_2CR^3$; —$NR^3{}_2$; —$N(R^3)C(O)R^3$; —$C(O)N(R^3)_2$; halogen; hydroxy; —$C(O)R^3$; arylalkyl; nitro; substituted or unsubstituted aryl;

(g) each $R^3$ is independently selected from the group consisting of hydrogen, substituted or unsubstituted alkyl having from 1–8 carbon atoms, and $R^9SR^6$;

(h) $R_5$ is selected from the group consisting of hydrogen; halogen; —$SR^6$; $R^9SR^6$; amino; hydroxy; and substituted or unsubstituted $C_1$–$C_8$ alkyl;

(i) each $R^6$ is independently selected from the group consisting of hydrogen; —$C(O)R^7$; —$C(S)R^7$; —$C(O)NR^7{}_2$; —$C(S)NR^7{}_2$; —$C(S)OR^7$; —$C(O)OR^7$; wherein $R^7$ is hydrogen or substituted or unsubstituted $C_1$–$C_8$ alkyl;

(j) each $R^8$ is independently selected from the group consisting of nil, substituted or unsubstitited alkyl having 1–35 carbon atoms, substituted or unsubstituted phenyl, benzyl, or $R^9SR^6$; and (k) $R^9$ is a substituted or unsubstituted $C_1$–$C_8$ alkyl.

2. A compound, according to claim 1, wherein Z is selected from the group consisting of imidazolium, thiazolium, oxazolium, pyrrolium, or pyrrolidinium.

3. A compound, according to claim 1, wherein Q is a single covelent bond or $NR^1$.

4. A compound, according to claim 1, wherein $R^1$ is independently selected from the group consisting of —$SR^6$; $R^9SR^6$; hydrogen; substituted or unsubstituted $C_1$–$C_8$ alkyl; $NR^3{}_2$; or —$CO_2R^3$.

5. A compound, according to claim 4, wherein $R^1$ is selected from the group consisting of —$SR^6$; $R^9SR^6$; or hydrogen.

6. A compound, according to claim 1, wherein $R^1$ is selected from the group consisting of —$SR^6$; $R^9SR^6$; hydrogen; substituted or unsubstituted $C_1$–$C_8$ alkyl; $NR^3{}_2$; —$OR^3$ or —$CO_2R^3$.

7. A compound, according to claim 6, wherein $R^2$ is selected from the group consisting of —$SR^6$; $R^9SR^6$; or hydrogen.

8. A compound, according to claim 1, wherein $R^3$ is selected from the group consisting of hydrogen; $R^9SR^6$; or substituted or unsubstituted $C_1$–$C_8$ alkyl.

9. A compound, according to claim 4, wherein $R^3$ is hydrogen; or $R^9SR^6$.

10. A compound, according to claim 8, wherein $R^3$ is hydrogen or $R^9SR^6$.

11. A compound, according to claim 4, wherein $R^6$ is selected from the group consisting of H; —$C(O)R^7$; $C(S)R^7$; or $C(O)N(R^7)_2$.

12. A compound, according to claim 11, wherein $R^6$ is selected from the group consisting of H; —$C(O)R^7$; or $C(S)R^7$.

13. A compound, according to claim 9, wherein $R^6$ is selected from the group consisting of H; —$C(O)R^7$; $C(S)R^7$; or $C(O) N(R^7)_2$.

14. A compound, according to claim 11, wherein $R^6$ is selected from the group consisting of H; —$C(O)R^7$; $C(S)R^7$; or $C(O) N(R^7)_2$.

15. A compound, according to claim 6, wherein $R^6$ is selected from the group consisting of H; —$C(O)R^7$; $C(S)R^7$; or $C(O)N(R^7)_2$.

16. A pharmaceutical composition comprising:

(a) a safe and effective amount of a quaternary nitrogen-containing phosphonate compound according to claim 1;

(b) a pharmaceutically-acceptable excipient.

17. A method for treating pathological conditions associated with abnormal calciumn or phosphate metabolism in humans or other mammals in need of such treatment, comprising administering to a human or other mammal a safe and effective amount of a quaternary nitrogen-containiing pliosplionate compound of claim 1.

18. A compound according to claim 1, wherein $R^8$ is an unsubstituted or substituted alkyl having 10 to 20 carbon atoms.

19. A compound according to claim 2, wherein each $R^2$ is independently selected from the group consisting of hydrogen, $C_1$–$C_8$ alkyl, $N^+(R^8)_3$, —$N(R^3)C(O)R^3$, $NR^3{}_2$, and phenylalkyl.

20. A compound according to claim 1, wherein each $R^1$ is independently selected from the group consisting of —$SR^6$, $R^9SR^6$, hydrogen, substituted or unsubstituted $C_1$–$C_8$ alkyl, $NR^3{}_2$, —$OR^3$, and $CO_2R^3$; $R^3$ is hydrogen or $R^9SR^6$; and $R^6$ is selected from the group consisting of H, —$C(O)R^7$, $C(S)R^7$, and $C(O)N(R^7)_2$.

21. A compound according to claim 2, wherein Z is imidazolium; and each $R^2$ is independently selected from the group consisting of hydrogen, $C_1$–$C_8$ alkyl, —$N(R^3)C(O)R^3$, $NR^3{}_2$, and arylalkyl wherein the aryl is phenyl.

22. A compound according to claim 2, wherein Z is oxazolium; and each $R^2$ is independently selected from the group consisting of hydrogen, $C_1$–$C_8$ alkyl, —$N(R^3)C(O)R^3$, $NR^3{}_2$, and arylalkyl wherein the aryl is phenyl.

23. A compound according to claim 2, wherein Z is thiazolium; and each $R^2$ is independently selected from the group consisting of hydrogen, $C_1$–$C_8$ alkyl, —N($R^3$)C(O)$R^3$, $NR^3{}_2$, and arylalkyl wherein the aryl is phenyl.

24. A compound according to claim 21, wherein each $R^1$ is independently selected from the group consisting of —$SR^6$, $R^9SR^6$, hydrogen, substituted or unsubstituted $C_1$–$C_8$ alkyl, $NR^3{}_2$, —$OR^3$, and $CO_2R^3$; $R^3$ is hydrogen, or $R^9SR^6$; and $R^6$ is selected from the group consisting of H, —C(O)$R^7$, C(S)$R^7$, and C(O)N($R^7)_2$.

25. A compound according to claim 22, wherein each $R^1$ is independently selected from the group consisting of —$SR^6$, $R^9SR^6$, hydrogen, substituted or unsubstituted $C_1$–$C_8$ alkyl, $NR^3{}_2$, —$OR^3$, and $CO_2R^3$; $R^3$ is hydrogen, or $R^9SR^6$; and $R^6$ is selected from the group consisting of H, —C(O)$R^7$, C(S)$R^7$, and C(O)N($R^7)_2$.

26. A compound according to claim 23, wherein each $R^1$ is independently selected from the group consisting of —$SR^6$, $R^9SR^6$, hydrogen, substituted or unsubstituted $C_1$–$C_8$ alkyl, $NR^3{}_2$, —$OR^3$, and $CO_2R^3$; $R^3$ is hydrogen, or $R^9SR^6$; and $R^6$ is selected from the group consisting of H, —C(O)$R^7$, C(S)$R^7$, and C(O)N($R^7)_2$.

27. A pharmaceutical composition comprising:

(a) a safe and effective amount of a quaternary nitrogen-containing phosphonate compound according to claim 20, and (b) a pharmaceutically-acceptable excipient.

28. A pharmaceutical composition comprising:

(a) a safe and effective amount of a quaternary nitrogen-containing phosphonate compound according to claim 24, and (b) a pharmaceutically-acceptable excipient.

29. A pharmaceutical composition comprising:

(a) a safe and effective amount of a quaternary nitrogen-containing phosphonate compound according to claim 25, and (b) a pharmaceutically-acceptable excipient.

30. A pharmaceutical composition comprising:

(a) a safe and effective amount of a quaternary nitrogen-containing phosphonate compound according to claim 26, and (b) a pharmaceutically-acceptable excipient.

31. A method for preventing pathological conditions associated with abnormal calcium or phosphate metabolism in humans or other mammals in need of such treatment, said method comprising:

(a) determining that abnormal calcium or phosphate metabolism occurs, or is likely to occur, in the human or other mammal; and (b) administering to the human or other mammal a safe and effective amount of a quaternary nitrogen-containing phosphonate compound of claim 1.

* * * * *